US010245131B2

(12) United States Patent
Cordasco

(10) Patent No.: US 10,245,131 B2
(45) Date of Patent: Apr. 2, 2019

(54) VERTICAL DIMENSION OF OCCLUSION JIGS USED IN ALL-ON-4 DENTAL PROCEDURES

(71) Applicant: John A. Cordasco, Rockaway, NJ (US)

(72) Inventor: John A. Cordasco, Rockaway, NJ (US)

( * ) Notice: Subject to any disclaimer, the term of this patent is extended or adjusted under 35 U.S.C. 154(b) by 0 days.

(21) Appl. No.: 15/635,840

(22) Filed: Jun. 28, 2017

(65) Prior Publication Data

US 2017/0367804 A1 Dec. 28, 2017

Related U.S. Application Data

(60) Provisional application No. 62/355,587, filed on Jun. 28, 2016, provisional application No. 62/426,351, filed on Nov. 25, 2016.

(51) Int. Cl.
*A61C 19/05* (2006.01)

(52) U.S. Cl.
CPC .................................. *A61C 19/05* (2013.01)

(58) Field of Classification Search
CPC ........... A61C 7/10; A61C 7/663; A61C 19/05; A61C 19/45; A61C 5/007; A61C 11/00; A61B 17/663; A61B 17/6433; A61B 17/8071; A61B 17/7041
USPC ..... 433/5, 7, 24, 68, 70, 73; 606/54, 56, 90, 606/105
See application file for complete search history.

(56) References Cited

U.S. PATENT DOCUMENTS

| | | | | |
|---|---|---|---|---|
| 3,024,534 A | * | 3/1962 | Wilkinson | A61C 19/05 433/73 |
| 4,662,365 A | * | 5/1987 | Gotzen | A61B 17/6483 606/54 |
| 6,171,313 B1 | * | 1/2001 | Razdolsky | A61B 17/666 433/7 |
| 7,220,262 B1 | * | 5/2007 | Hynes | A61B 17/7011 606/279 |
| 7,473,269 B1 | * | 1/2009 | Hynes | A61B 17/7011 606/250 |
| 7,485,121 B2 | * | 2/2009 | Noon | A61B 17/66 606/90 |

(Continued)

FOREIGN PATENT DOCUMENTS

WO WO 2013054157 A1 * 4/2013 ............ A16B 17/66

*Primary Examiner* — Wade Miles
*Assistant Examiner* — Matthew P Saunders
(74) *Attorney, Agent, or Firm* — Doherty IP Law Group LLC

(57) ABSTRACT

A vertical dimension of occlusion jig includes a vertical support column, a lateral arm support base configured to slide along and rotate about a longitudinal axis of the vertical support column, a first lateral support arm pivotally coupled with the lateral arm support base, a first tooth gantry coupled with the first lateral support arm and adapted to slide along and rotate about a longitudinal axis of the first lateral support arm, a second lateral support arm pivotally coupled with the lateral arm support base, and a second tooth gantry coupled with the second lateral support arm and adapted to slide along and rotate about a longitudinal axis of the second lateral support arm. A temporary anchorage device (TAD) gantry is coupled with the vertical support column and is configured to slide along a longitudinal axis that is perpendicular to the longitudinal axis of the vertical support column.

20 Claims, 29 Drawing Sheets

(56) References Cited

U.S. PATENT DOCUMENTS

| | | | | |
|---|---|---|---|---|
| 8,662,889 B2* | 3/2014 | Baker | ...................... | A61C 7/00 433/18 |
| 2003/0138755 A1* | 7/2003 | Tremont | .............. | A61C 19/045 433/68 |
| 2003/0229345 A1* | 12/2003 | Stahurski | ........... | A61B 17/7035 606/310 |
| 2004/0166467 A1* | 8/2004 | Crow | ..................... | A61C 19/05 433/49 |
| 2004/0166470 A1* | 8/2004 | Crow | ..................... | A61C 19/05 433/70 |
| 2009/0131944 A1* | 5/2009 | Noon | ..................... | A61B 17/66 606/90 |
| 2016/0095625 A1* | 4/2016 | Sanders | ................. | A61B 17/60 606/54 |

* cited by examiner

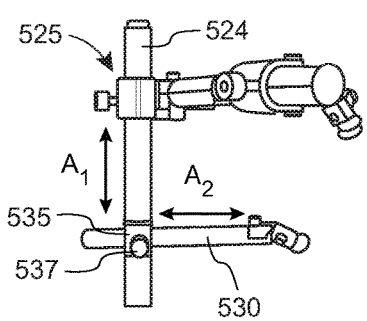
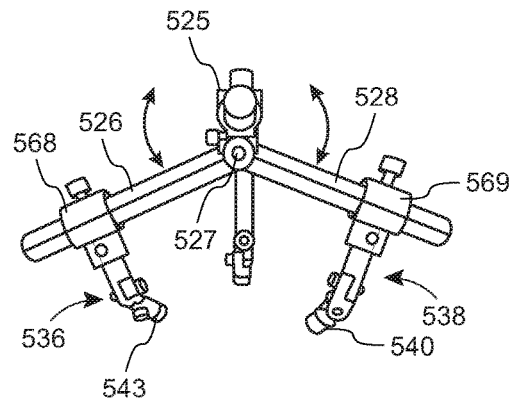
FIG. 28  FIG. 29
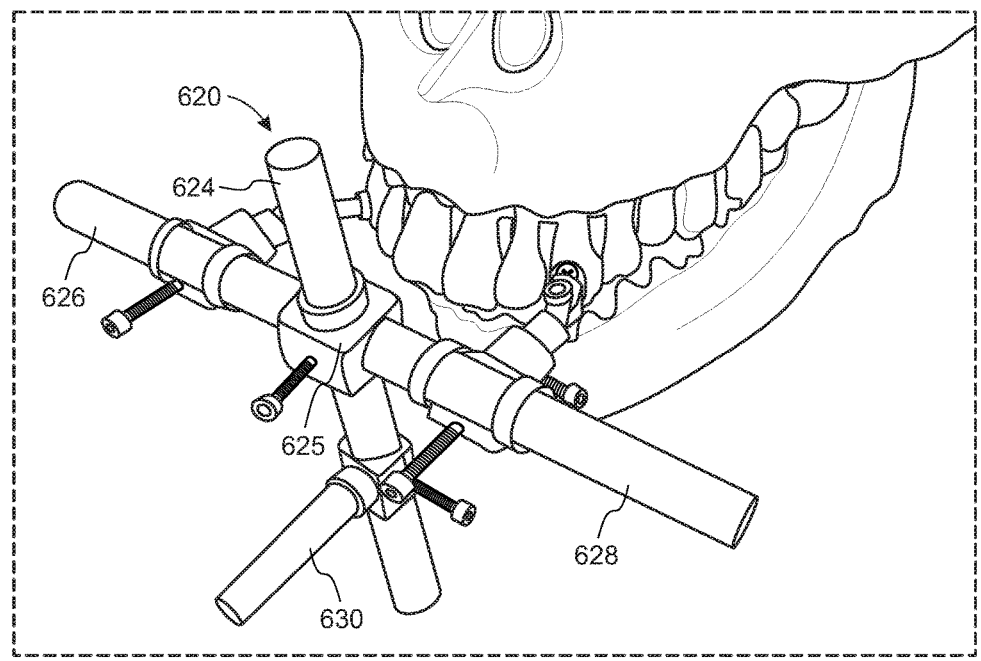
FIG. 30

VERTICAL DIMENSION OF OCCLUSION JIGS USED IN ALL-ON-4 DENTAL PROCEDURES

CROSS-REFERENCE TO RELATED APPLICATIONS

The present patent application claims benefit of U.S. Provisional Application Ser. No. 62/355,587, filed Jun. 28, 2016, and U.S. Provisional Application Ser. No. 62/426,351, filed Nov. 25, 2016, the disclosures of which are hereby incorporated by reference herein.

BACKGROUND OF THE INVENTION

Field of the Invention

The present patent application is generally directed to dentistry and is more particularly directed to medical devices, tools and procedures used during All-On-4 prosthodontic procedures in which dentures are supported on dental implants.

Description of the Related Art

The term All-On-4 refers to a prosthodontics procedure in which all of the maxillary or mandibular teeth of a patient are supported on four dental implants. The All-On-4 procedure is used for the total rehabilitation of an edentulous patient or for patients with badly broken down teeth, decayed teeth, or teeth that have been compromised due to gum disease. The procedure includes the rehabilitation of either edentulous or dentate maxilla and/or mandible with a fixed denture prosthesis by placing four implants in the anterior maxilla and/or mandible, where bone density is higher. The four implants support a fixed denture prosthesis having approximately 10-14 teeth. The denture prosthesis is typically placed immediately or within 24 hours of surgery. See https://en.wikipedia.org/wiki/All-on-4.

The All-on-4 procedure is preferred for patients with significant tooth loss or decay and for people whose bone loss in the jaw area prevents them from receiving conventionally oriented (i.e., vertical) dental implants. Often, tooth loss is accompanied by bone loss in the maxilla or mandible, which poses jaw bone reconstruction problems that require bone grafting. The All-On-4 procedure is a graft-less solution that avoids the lengthy ordeal of rebuilding bone that is required when conventionally oriented implants are used.

To insure the success of the All-On-4 procedure, a careful analysis of the bone structure is typically made before the surgical procedure commences. One way to evaluate the bone is by using a CBCT scan. During the All-On-4 procedure, at least four implants are placed in a jaw bone. The back implants are typically angled at approximately 30 to 45 degrees from the biting plane. The implants are placed in front of the maxillary sinus in the maxilla (i.e., the upper jaw) and in front of the mental nerve in the mandible (i.e., the lower jaw). The head of the implant emerges in approximately the second premolar position, which allows a molar tooth to be cantilevered posterior and resulting in a denture or bridge with approximately 10-14 teeth.

The All-On-4 procedure requires a dental surgeon to consider a patient's vertical dimension of occlusion, also referred to as VDO. Vertical dimension of occlusion is a term used in dentistry to indicate the superior-inferior relationship of the maxilla and the mandible when the teeth are situated in maximum intercuspation. Harper, R P; Misch, C E: *Current Topics in Dentistry, Quintessence International,* 31:4 (April 2000).

A VDO is not only possessed by people who have teeth. For completely edentulous individuals who do not have any teeth with which to position themselves in maximum intercuspation, VDO can be measured based on subjective signs related to aesthetics and phonetics.

In terms of aesthetics, an appropriately measured VDO will appear to a layman's eye as an ordinary configuration of the patient's nose, lips and chin. An excessive VDO will appear as though the patient has something stuffed into their mouth, and the patient may not even be able to close his or her lips. A telltale indication of an excessive VDO is a patient straining to close his or her lips around wax rims used during VDO determination. Conversely, a deficient VDO will appear as though the patient's mouth has collapsed, and the chin appears too close to the nose.

In terms of phonetics, certain sounds are made by configuring the mouth in specific ways. The two sounds most commonly used to establish a patient's VDO are sibilant and fricative sounds. Sibiliant sounds are made by allowing the maxillary incisors to nearly touch the mandibular incisors, while fricative sounds are made by allowing the maxillary incisors to touch the slightly inverted lower lip at the wet-dry line. By having the patient count upwards from fifty and then upwards from sixty, the dentist can watch and listen to the patient attempting to make first fricative and then sibilant sounds and adjust the wax rims accordingly.

A common tool used by dentists is to ask a patient to say the name "Emma," as the position of the mandible immediately after completing the word is a rough estimate of the patient's proper VDO. The position after saying "Emma" is referred to as the vertical dimension at rest, or VDR. Historically, the VDO has been estimated at 3 mm less than VDR because a person will generally maintain their mandible at an opening of 3 mm when at rest. Bhat, V S; M Gopinathan, M: *Reliability of determining vertical dimension of occlusion in complete dentures: A clinical study,* JIPS, 6:1:38-42 (2006).

Another practical way to find a suitable VDO is to take the distance between the corner of a patient's eye and the corner of the patient's lips, and comparing the measurement to the distance between the bottom of the patient's nose and the bottom of the patient's chin. According to the Golden Proportion principle, an individual is considered to be more attractive when the distance between the corner of the eye and the corner of the mouth matches the distance between the bottom of the nose and the bottom of the chin. Dental surgeons attempt to have these distances match during All-On-4 procedures.

Referring to FIG. 32, one conventional way of recording a patient's pre-surgical VDO is to affix a first sticker 802 on the patient's nose and a second sticker 304 on the patient's chin. Dots 806A, 806B are drawn on the two stickers 802, 804 to record the patient's VDO before the All-On-4 procedure is commenced. After all of the patient's maxilla or mandibular teeth have been removed, the dots 806A, 806B are used by the dentist to restore the VDO. Unfortunately, swelling of the patient's face, blood, and bodily fluid, may cause the position of the dots to change and/or the dots to distort, which will make it difficult for the dentist to replicate the patient's previously recorded VDO.

Thus, there remains a need for medical devices, tools and methods that more accurately record a patient's VDO prior to All-On-4 surgery, and that enable an oral surgeon to restore the patient's proper VDO when inserting dental implants and dentures.

SUMMARY OF THE INVENTION

In one embodiment, an All-On-4 vertical dimension of occlusion (VDO) jig is used to establish and allow changes and adjustments to the vertical dimension of occlusion of a patient once the last vestige of vertical dimension is removed through the extraction of all remaining teeth in the surgical arch and the subsequent obliteration of the remaining alveolar crest prior to placement of dental implants.

In one embodiment, the All-On-4 procedure is accomplished by placing two or three fixed points between the arches to which the VDO jig will be fastened, thereby recording the pre-surgery VDO information and allowing for adjustments equivalent to that which is made in the laboratory during the creation of a denture prosthetic, which will eventually be converted into the All-On-4 interim appliance.

In one embodiment, a vertical dimension of occlusion (VDO) jig used in all-on-4 dental procedures desirably includes a vertical support column having an upper end, a lower end, and a longitudinal axis that extends between the upper and lower ends, a lateral arm support base coupled with the vertical support column, the lateral arm support base being configured to slide along and rotate about the longitudinal axis of the vertical support column.

In one embodiment, a VDO jig includes a first lateral support arm having a proximal end pivotally coupled with the lateral arm support base, a distal end spaced from the proximal end, and a longitudinal axis extending between the proximal and distal ends thereof, and a first tooth gantry having a proximal end coupled with the first lateral support arm and a distal end spaced therefrom, wherein the proximal end of the first tooth gantry is adapted to slide along and rotate about the longitudinal axis of the first lateral support arm.

In one embodiment a VDO jig includes a second lateral support arm having a proximal end pivotally coupled with the lateral arm support base, a distal end spaced from the proximal end, and a longitudinal axis extending between the proximal and distal ends thereof, and a second tooth gantry having a proximal end coupled with the second lateral support arm and a distal end spaced therefrom, wherein the proximal end of the second tooth gantry is adapted to slide along and rotate about the longitudinal axis of the second lateral support arm.

In one embodiment, a VDO jig includes a temporary anchorage device (TAD) gantry coupled with the vertical support column. In one embodiment the TAD gantry has a shaft that is configured to slide along a longitudinal axis that is perpendicular to the longitudinal axis of the vertical support column.

In one embodiment, a VDO jig includes a lateral arm support base fastener having a first position in which the lateral arm support base is free to slide along and rotate relative to the longitudinal axis of the vertical support column and a second position in which the lateral arm support base is locked in position and prevented from sliding along and rotating relative to the longitudinal axis of the vertical support column.

In one embodiment, a VDO jig has a lateral support arm fastener having a first position in which the first and second lateral support arms are free to pivot relative to the lateral arm support base and a second position in which the first and second lateral support arms are locked in place and prevented from pivoting relative to the lateral arm support base.

In one embodiment, a VDO jig includes a TAD gantry fastener having a first position in which the TAD gantry shaft is free to slide along the longitudinal axis that is perpendicular to the longitudinal axis of the vertical support column and a second position in which the TAD gantry shaft is locked in place and prevented from sliding along the longitudinal axis that is perpendicular to the longitudinal axis of the vertical support column.

In one embodiment, the proximal end of the first tooth gantry has a first tooth gantry base coupled with the first lateral support arm. In one embodiment, the first tooth gantry includes a first tooth gantry base fastener having a first position in which the first tooth gantry base is free to slide along and rotate about the longitudinal axis of the first lateral support arm and a second position in which the first tooth gantry base is locked in place and prevented from sliding along and rotating about the longitudinal axis of the first lateral support arm.

In one embodiment, the first tooth gantry may include a first tooth gantry shaft coupled with the first tooth gantry base, and a first tooth gantry shaft fastener having a first position in which the first tooth gantry shaft is extendable and retractable relative to the first tooth gantry base and a second position in which the first tooth gantry shaft is locked in place and is prevented from extending and retracting relative to the first tooth gantry base.

In one embodiment, a VDO jig includes a first tooth gantry socket coupled with a distal end of the first tooth gantry shaft. In one embodiment, a first universal joint connects the first tooth gantry socket with the distal end of the first tooth gantry shaft for enabling the first tooth gantry socket to rotate and pivot relative to the distal end of the first tooth gantry shaft.

In one embodiment, a VDO jig includes a first universal joint fastener for the first tooth gantry socket having a first position in which the first tooth gantry socket is free to pivot relative to the distal end of the first tooth gantry shaft and a second position in which the first tooth gantry socket is locked in place and prevented from pivoting relative to the distal end of the first tooth gantry shaft.

In one embodiment, a VDO jig includes a second universal joint fastener for the first tooth gantry socket having a first position in which the first tooth gantry socket is free to rotate relative to the distal end of the first tooth gantry shaft and a second position in which the first tooth gantry socket is locked in place and prevented from rotating relative to the distal end of the first tooth gantry shaft.

In one embodiment, the proximal end of the second tooth gantry has a second tooth gantry base coupled with the second lateral support arm. In one embodiment, the second tooth gantry includes a second tooth gantry base fastener having a first position in which the second tooth gantry base is free to slide along and rotate about the longitudinal axis of the second lateral support arm and a second position in which the second tooth gantry base is locked in place and prevented from sliding along and rotating about the longitudinal axis of the second lateral support arm.

In one embodiment, the second tooth gantry may include a second tooth gantry shaft coupled with the second tooth gantry base, and a second tooth gantry shaft fastener having a first position in which the second tooth gantry shaft is extendable and retractable relative to the second tooth gantry base and a second position in which the second tooth gantry shaft is locked in place and is prevented from extending and retracting relative to the second tooth gantry base.

In one embodiment, a VDO jig includes a second tooth gantry socket coupled with a distal end of the second tooth gantry shaft, and a second universal joint connecting the second tooth gantry socket with the distal end of the second tooth gantry shaft for enabling the second tooth gantry socket to rotate and pivot relative to the distal end of the second tooth gantry shaft.

In one embodiment, a VDO jig may include a first universal joint fastener for the second tooth gantry socket having a first position in which the second tooth gantry socket is free to pivot relative to the distal end of the second tooth gantry shaft and a second position in which the second tooth gantry socket is locked in place and prevented from pivoting relative to the distal end of the second tooth gantry shaft.

In one embodiment, a VDO jig may include a second universal joint fastener for the second tooth gantry socket having a first position in which the first tooth gantry socket is free to rotate relative to the distal end of the first tooth gantry shaft and a second position in which the first tooth gantry socket is locked in place and prevented from rotating relative to the distal end of the first tooth gantry shaft.

In one embodiment, a TAD gantry may include a TAD gantry socket coupled with a distal end of the TAD gantry shaft, and a TAD gantry universal joint connecting the TAD gantry socket with the distal end of the TAD gantry shaft for enabling the TAD gantry socket to rotate and pivot relative to the distal end of the TAD gantry shaft.

In one embodiment, a VDO jig may have a first universal joint fastener for the TAD gantry socket having a first position in which the TAD gantry socket is free to pivot relative to the distal end of the TAD gantry shaft and a second position in which the TAD gantry socket is locked in place and prevented from pivoting relative to the distal end of the TAD gantry shaft.

In one embodiment, a VDO jig may include a second universal joint fastener for the TAD gantry socket having a first position in which the TAD gantry socket is free to rotate relative to the distal end of the TAD gantry shaft and a second position in which the TAD gantry socket is locked in place and prevented from rotating relative to the distal end of the TAD gantry shaft.

In one embodiment, the vertical distance between the lateral arm support base and the TAD gantry is adjustable when the lateral arm support base fastener is in the first position and is not adjustable when the lateral arm support base fastener is in the second position.

In one embodiment, a VDO jig may be made of metals such as steel, stainless steel, aluminum, titanium and alloys thereof and polymers.

In one embodiment, a VDO jig may include a ball component attached to a tooth, such as by using an adhesive, whereby the first tooth gantry socket is connected to the ball component for releasably securing the first tooth gantry to the tooth.

In one embodiment, the second tooth gantry socket may be connected to a ball attached to another tooth, and the TAD gantry socket may be connected to a ball component attached to a bone or a mandible of a patient.

These and other preferred embodiments of the present invention will be described in more detail below.

BRIEF DESCRIPTION OF THE DRAWINGS

FIG. 23B shows a bottom view of the VDO jig of FIG. 19 secured to a patient, in accordance with one embodiment of the present invention.

FIG. 28 shows a side view of the VDO jig of FIG. 25.

FIG. 29 shows a top view of the VDO jig of FIG. 25.

FIG. 30 shows a perspective view of a vertical dimension of occlusion (VDO) jig, in accordance with another embodiment.

DETAILED DESCRIPTION

Figure 1:
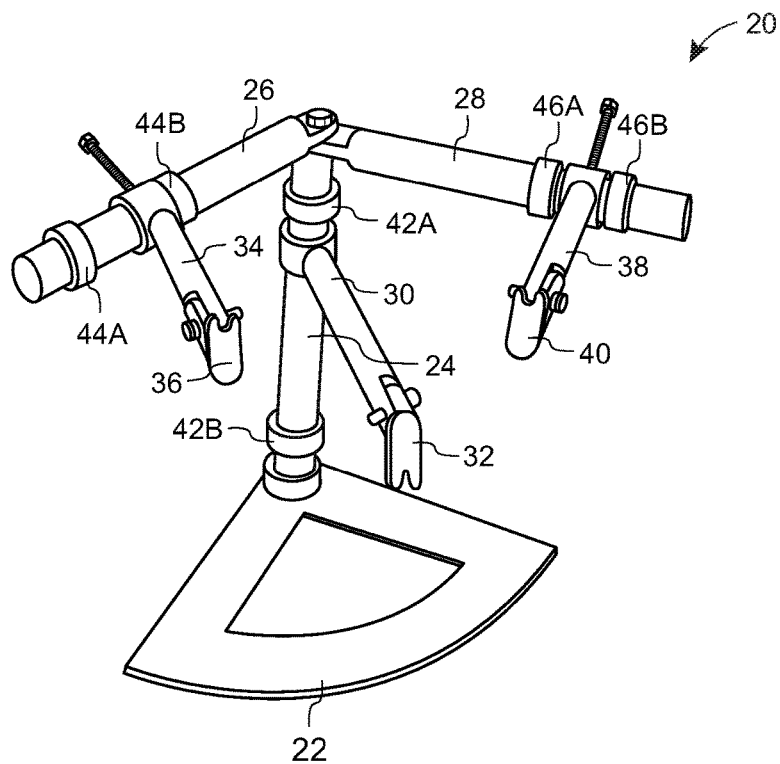
FIG. 1 shows a perspective view of a vertical dimension of occlusion (VDO) jig including a support base, a vertical support column, first and second lateral support arms, a temporary anchorage device (TAD) gantry, three engagement swivels, and first and second tooth gantries, in accordance with one embodiment of the present invention.

Referring to FIG. 1, in one embodiment, a vertical dimension of occlusion (VDO) jig 20 preferably includes a support base 22 and a vertical support column 24 that extends upwardly from the support base 22. The VDO jig 20 also includes a first lateral support arm 26 and a second lateral support arm 28 that are pivotally connected to an upper end of the vertical support column 24. In one embodiment, the VDO jig 20 includes a temporary anchorage device (TAD) gantry 30 that is coupled with the vertical support column 24 and that is adapted to swing about the vertical support column and be adjustable up and down the vertical height of the vertical support column. In one embodiment, the VDO jig 20 includes an engagement swivel 32 that is pivotally coupled with the distal end of the TAD gantry 30.

In one embodiment, the VDO jig 20 includes a first tooth gantry 34 that is coupled with the first lateral support arm 26. An engagement swivel 36 is pivotally connected with the distal end of the first tooth gantry 34. In one embodiment, the VDO jig 20 preferably includes a second tooth gantry 38 connected with the second lateral support arm 28. An engagement swivel 40 is pivotally connected with a distal end of the second tooth gantry 38.

In one embodiment, the VDO jig 20 includes a first pair of adjustment rings 42A, 42B provided on the vertical support column 24 for making vertical adjustments of the TAD gantry 30 relative to the vertical support column 24, or for confirming and recording the position of the TAD gantry on the vertical support column. The VDO jig 20 preferably includes a pair of adjustment rings 44A, 44B provided on the first lateral support arm 26 for making lateral adjustments of the tooth gantry 34 relative to the first lateral support arm 26. In one embodiment, the VDO jig 20 also desirably includes a set of alignment rings 46A, 46B provided on the second lateral support arm 28 for making lateral adjustments of the second tooth gantry 38 relative to the second lateral support arm 28, or confirming and recording the position of the tooth gantry relative to the lateral support arm.

In one embodiment, the TAD gantry 30 is adapted to swing about the vertical support column 24 and move up and down the length of the vertical support column 24. The engagement swivel 32 coupled with the distal end of the TAD gantry 30 is adapted to pivot relative to the distal end of the TAD gantry 30 for conforming to the angle of inclination of an opposing tooth.

Figures 2, 3:
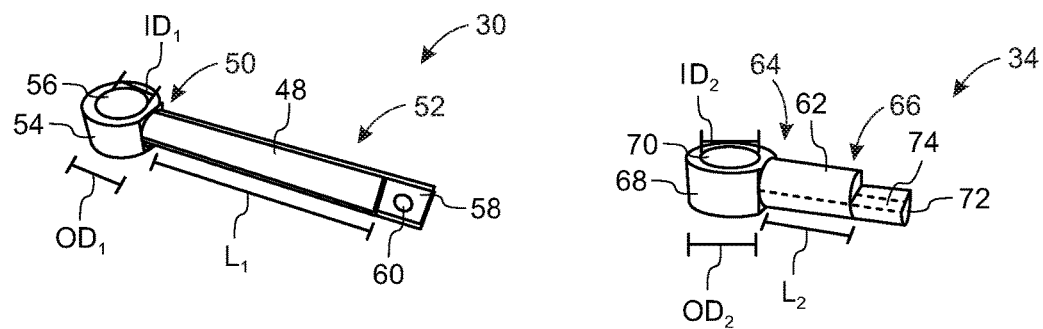
FIG. 2 shows a perspective view of the temporary anchorage device (TAD) gantry of FIG. 1, in accordance with one embodiment of the present invention.
FIG. 3 shows a perspective view of the first tooth gantry of FIG. 1, in accordance with one embodiment of the present invention.

Referring to FIG. 2, in one embodiment, the TAD gantry 30 preferably includes an elongated shaft 48 having a proximal end 50 and a distal end 52. The TAD gantry 30 has a length $L_1$ that extends between the proximal end 50 and the distal end 52 of the shaft 48. In one embodiment, a ring 54 having a central opening 56 is attached to the proximal end 50 of the elongated shaft 48. In one embodiment, the central opening 56 of the ring 54 slides over the outer surface of the vertical support column 24 (FIG. 1). In one embodiment, the ring 54 has an outer diameter $OD_1$ of about 10 mm and the central opening has an inner diameter $ID_1$ of about 7 mm that closely matches the outer diameter of the vertical support column.

In one embodiment, the TAD gantry 30 includes an attachment flange 58 having an opening 60 that facilitates forming a pivotal coupling between an engagement swivel 32 (FIG. 1) and the attachment flange 58 of the TAD gantry 30.

Referring to FIG. 3, in one embodiment, the VDO jig 20 also includes the tooth gantry 34 having a shaft 62 with a length $L_2$ that extends from a proximal end 64 to a distal end 66. The tooth gantry 34 includes a ring 68 having a central opening 70 that is attached to the proximal end 64 of the shaft 62. The tooth gantry 34 includes an attachment flange 72 secured to the distal end 66 of the shaft 62. The attachment flange 72 includes an opening 74 adapted to provide a pivot connection between the engagement swivel 36 (FIG. 1) and the attachment flange 72. In one embodiment, the ring 68 of the tooth gantry 34 has an outer diameter $OD_2$ of about 10 millimeters, and the central opening 70 of the ring 82 has an inner diameter $ID_2$ of about 7 millimeters that closely matches the outer diameter of the lateral support arms.

In one embodiment, the engagement swivels are pivotally coupled with the distal ends of the tooth gantries, respectively, and the rings 68 at the proximal ends of the tooth gantries are coupled with the lateral support arms 26, 28 (FIG. 1). The distal ends of the tooth gantries are adapted to swing about the lateral support arms to provide vertical movement that enables engagement with the orthodontic brackets or other attachment device affixed on the patient's teeth. The pivotal connection with the engagement swivels allows the engagement swivels to align with the axial inclination of the opposing teeth.

Figure 4:
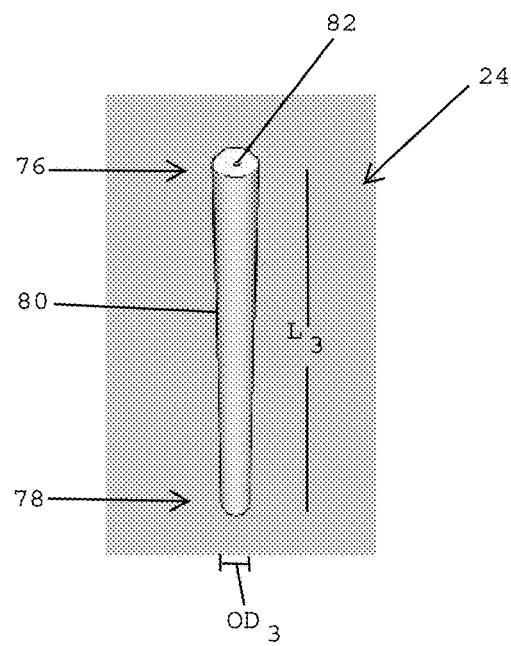
FIG. 4 shows a perspective view of the vertical support column of FIG. 1, in accordance with one embodiment of the present invention.

Referring to FIG. 4, in one embodiment, the VDO jig 20 (FIG. 1) has the vertical support column 24 having an upper end 76 and a lower end 78. In one embodiment, the vertical support column 24 has an elongated shaft 80 with a cylindrical-shaped cross section that extends from the upper end 76 and the lower end 78. The vertical support column 24 preferably includes a threaded opening 82 provided at the upper-most end of the elongated shaft 80, which is utilized for forming a swing connection between proximal ends of the first and second lateral support arms 26, 28 (FIG. 1) and the upper end 76 of the vertical support column 24. In one embodiment, the lower end 78 of the shaft 80 of the vertical support column 24 is inserted into a receptacle provided on the support base 22 of the VDO jig 20 (FIG. 1).

In one embodiment, the cylindrical-shaped shaft 80 of the vertical support column 24 has an outer diameter $OD_3$ of about 7 millimeters. In one embodiment, the shaft 80 has a length $L_3$ of about 50 millimeters.

The vertical support column 24 is adapted to be coupled with the lateral support arms. In one embodiment, the vertical support column acts as the pivot for the lateral support arms so that the lateral support arms can compensate for the curvature of the arch with the natural teeth remaining. The vertical support column also serves as the hand support for the entire VDO jig and as a rotational support for the TAD gantry 30 (FIG. 1).

Figure 5:
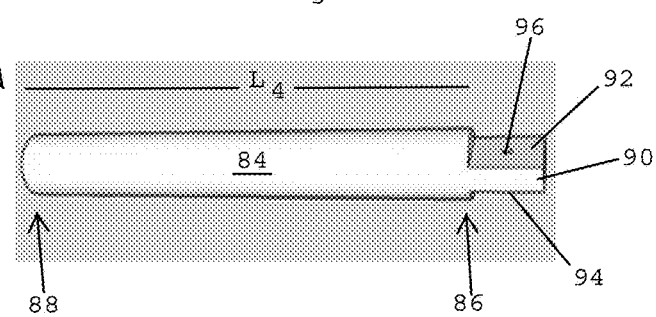
FIG. 5 shows a perspective view of the first lateral support arm of FIG. 1, in accordance with one embodiment of the present invention.

Referring to FIG. 5, in one embodiment, the VDO jig 20 (FIG. 1) has the first lateral support arm 26 including an elongated shaft 84 having a proximal end 86 and a distal end 88. In one embodiment, the shaft 84 has a length $L_4$ of about 40 millimeters. The first lateral support arm 26 includes an attachment flange 90 secured to the proximal end 86 of the shaft 84. The attachment flange 90 has an upper flat surface 92 and a lower flat surface 94 with an opening 96 extending from the upper flat surface 92 and the lower flat surface 94. The opening 96 in the attachment flange 90 enables the proximal end 86 of the shaft 84 of the first lateral support arm to be pivotally connected with the upper end 76 of the vertical support column 24 (FIG. 4). In one embodiment, a threaded fastener is used for connecting the proximal end 86 of the shaft 84 with the upper end of the vertical support column. In one embodiment, the second lateral support arm 28 (FIG. 1) has a similar structure.

In one embodiment, the VDO jig has two lateral support arms. In one embodiment, proximal ends of the lateral support arms are coupled with the upper end of the vertical support column and tooth gantries are assembled with the shafts of the respective lateral support arms. The swinging movement of the distal ends of the lateral support arms enables the arms to match the curvature of the opposing arch. The lateral support arms also act as the pivot base for the tooth gantries, thus allowing compensation for the axial inclination of the natural teeth.

Figure 6:
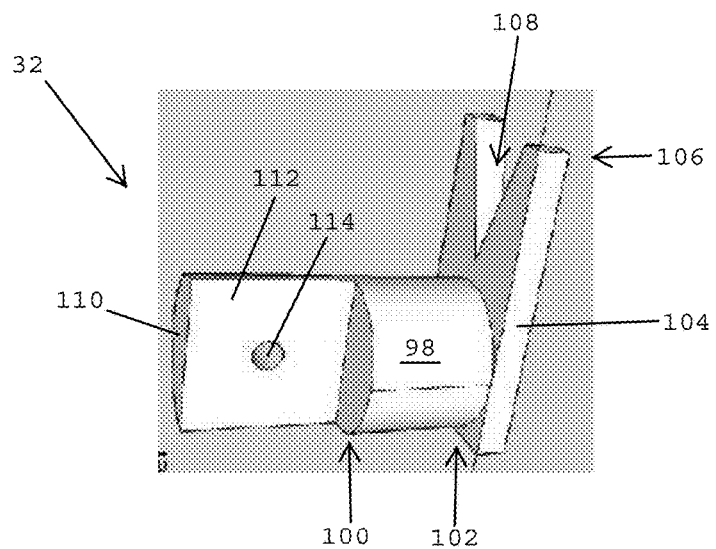
FIG. 6 shows a perspective view of a first one of the engagement swivels of FIG. 1, in accordance with one embodiment of the present invention.

Referring to FIG. 6, in one embodiment, the VDO jig includes one or more engagement swivels 32 that may be pivotally connected with the distal ends of the TAD gantry 30 (FIG. 2) and the respective first and second tooth gantries 34, 38 (FIG. 1). In one embodiment, the engagement swivel 32 includes a shaft 98 having a proximal end 100 and a distal end 102. The engagement swivel 32 includes an engagement flange 104 provided at the distal end 102 of the shaft 98. In one embodiment, the engagement flange 104 has a distal end 106 with a v-shaped notch 108 that is cut into the distal end 106. The engagement swivel 32 desirably includes an attachment flange 110 secured to the proximal end 100 of the shaft 98. The attachment flange 110 includes a flat surface 112 and an opening 114 that extends through the thickness of the attachment flange 110 for forming a pivotal connection with a distal end of a TAD gantry 30 (FIG. 2) or a distal end of a tooth gantry 34 (FIG. 3).

In one embodiment, the VDO jig has three engagement swivels. In one embodiment, the engagement swivels allow for the direct attachment of the VDO jig to both a fixed attachment on a natural tooth, such as an orthodontic bracket or other bonded device, and a Temporary Anchorage Device (TAD) fixed into the bone of the arch from which teeth will be removed. Each engagement swivel is adapted to pivot about the distal ends of the teeth gantries and/or the TAD gantry to allow the engagement swivels to match the axial inclinations of the existing teeth or opposing bone. In one embodiment, the engagement swivels may be fastened to the orthodontic brackets and the TADs using securing elements such as elastics, rubber bands, and/or orthodontic ligature wire.

The configuration of the engagement swivel may be changed to adapt to numerous other attachment apparatus shapes such as loop and hook and/or ball and socket attachments.

Figure 7A:
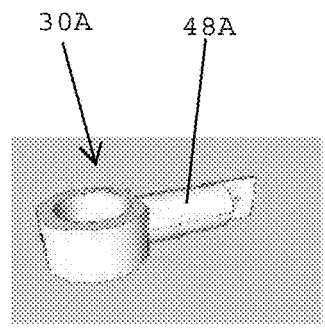
FIG. 7A shows a perspective view of a temporary anchorage device (TAD) gantry, in accordance with one embodiment of the present invention.
Figure 7B:
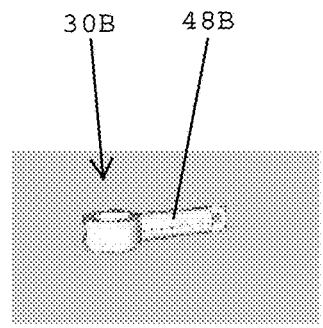
FIG. 7B shows a perspective view of a second temporary anchorage device (TAD) gantry, in accordance with one embodiment of the present invention.
Figure 7C:
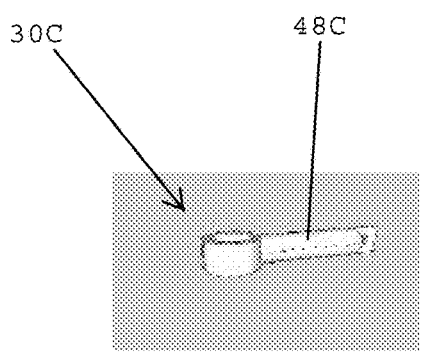
FIG. 7C shows a perspective views of a third temporary anchorage device (TAD) gantry, in accordance with one embodiment of the present invention.
Figure 7D:
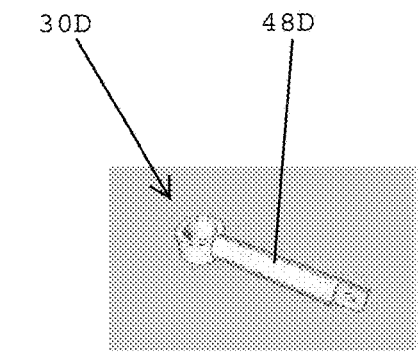
FIG. 7D shows a perspective views of fourth temporary anchorage device (TAD) gantry, in accordance with one embodiment of the present invention.
Figure 7E:
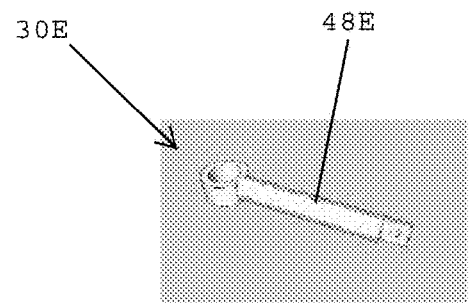
FIG. 7E shows a perspective views of fifth temporary anchorage device (TAD) gantry, in accordance with one embodiment of the present invention.

Referring to FIG. 7A-7E, in one embodiment, the TAD gantries 30 may have shafts 48 having different lengths. Referring to FIG. 7A, in one embodiment, a TAD gantry 30A has an elongated shaft 48A having a length of approximately 15 millimeters. Referring to FIG. 7B, in one embodiment, a TAD gantry 30B has a shaft 48B having a length of approximately 20 millimeters. Referring to FIG. 7C, in one embodiment, a TAD gantry 30C has a shaft 48C having a length of about 25 millimeters. Referring to FIG. 7D, in one embodiment, a TAD gantry 30D has a shaft 48D having a length of about 30 millimeters. Referring to FIG. 7E, in one embodiment, a TAD gantry 30E has a shaft 48E having a length of about 35 millimeters. The various shaft lengths (e.g., 15, 20, 25, 30 and 35 mm lengths) allow the VDO jig to be used on patients having various (+/−) overjets, as will be described in more detail herein. The various shaft lengths may also be used to accommodate different angles between the first and second lateral support arms. Generally, obtuse angles between the first and second lateral support arms will require the use of TAD gantries having shorter lengths, and more acute angles between the first and second lateral support arms will require the use of TAD gantries having greater lengths.

The VDO jig disclosed herein is designed to establish, record, and allow for changes to the vertical dimension of occlusion once one or more components of vertical dimension of a patient is removed, such as through the extraction of all remaining teeth in a surgical arch and the subsequent obliteration of the remaining alveolar crest prior to placement of dental implants. In one embodiment, this is accomplished by placing three fixed points between the arches to which the VDO jig will be fastened, thereby recording and retaining the vertical dimension of occlusion information and allowing for VDO adjustments made in the laboratory during the creation of a denture prosthetic.

Figure 8:
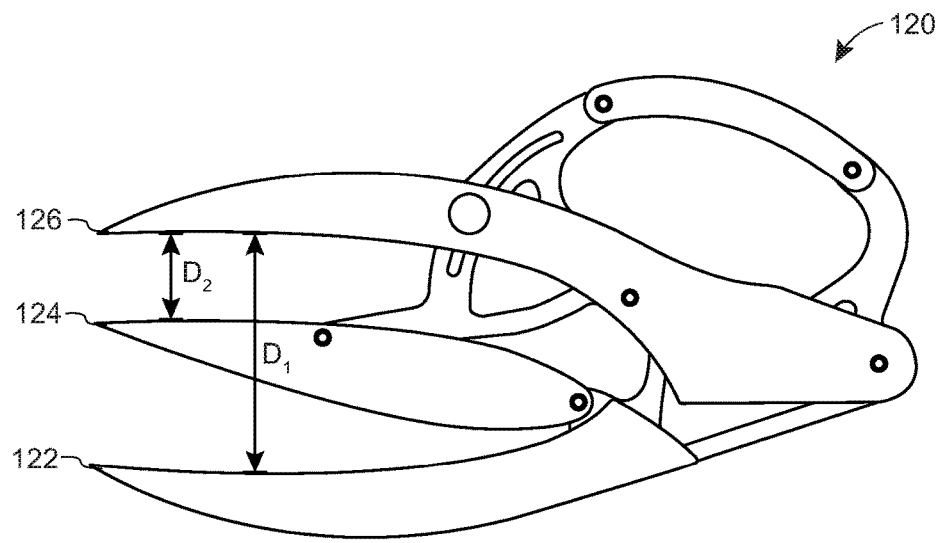
FIG. 8 shows a front elevation view of a caliper measuring device for determining orofacial dimensions, in accordance with one embodiment of the present invention.

Referring to FIG. 8, in one embodiment, a caliper 120 is used for determining orofacial dimensions. In one embodiment, the caliper 120 is used for recording vertical dimensions, including the dimensions associated with the Golden Proportion principle. The caliper 120 assists medical personnel in obtaining vertical dimension of occlusion information and making necessary adjustments so that the final facial features comport with the preferred Golden Proportion principle. In one embodiment, the caliper 120 includes a first point 122, a second point 124, and a third point 126. In one embodiment, the distance $D_1$ between the first point 122 and the third point 126 is 1.0 and the distance $D_2$ between the second point 124 and the third point 126 is 0.38.

Figure 9A:
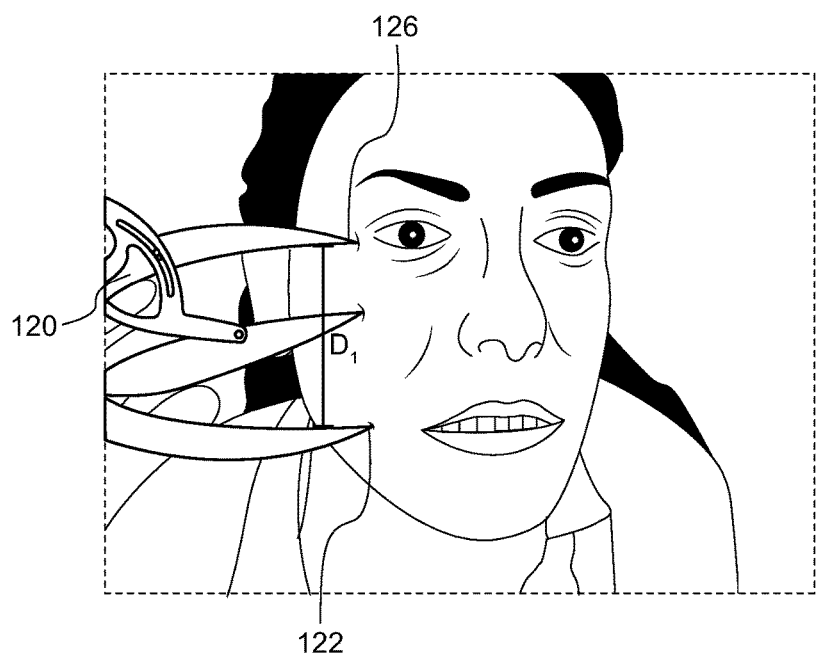
FIG. 9A shows a first step of a method of using the caliper measuring device shown in FIG. 8.
Figure 9B:
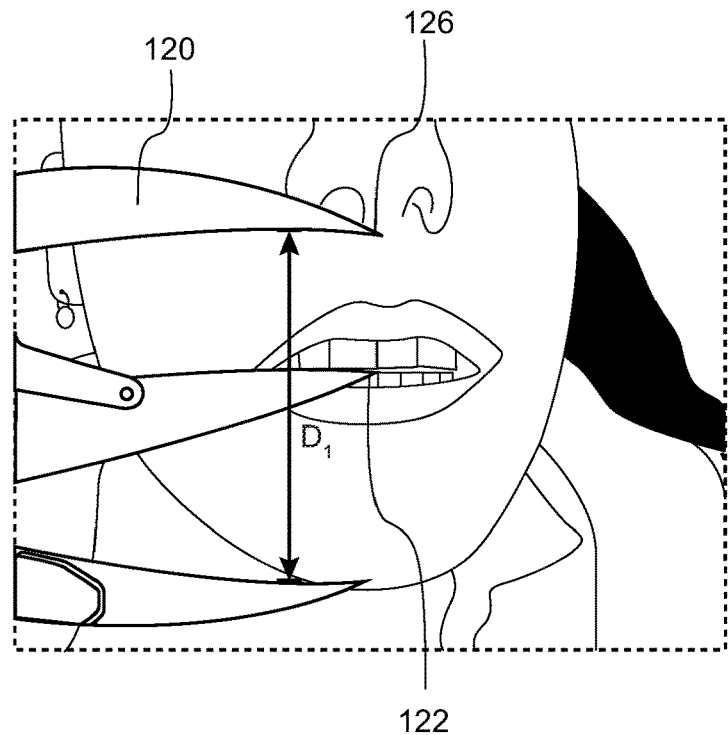
FIG. 9B shows a second step of a method of using the caliper measuring device shown in FIG. 8.
Figure 9C:
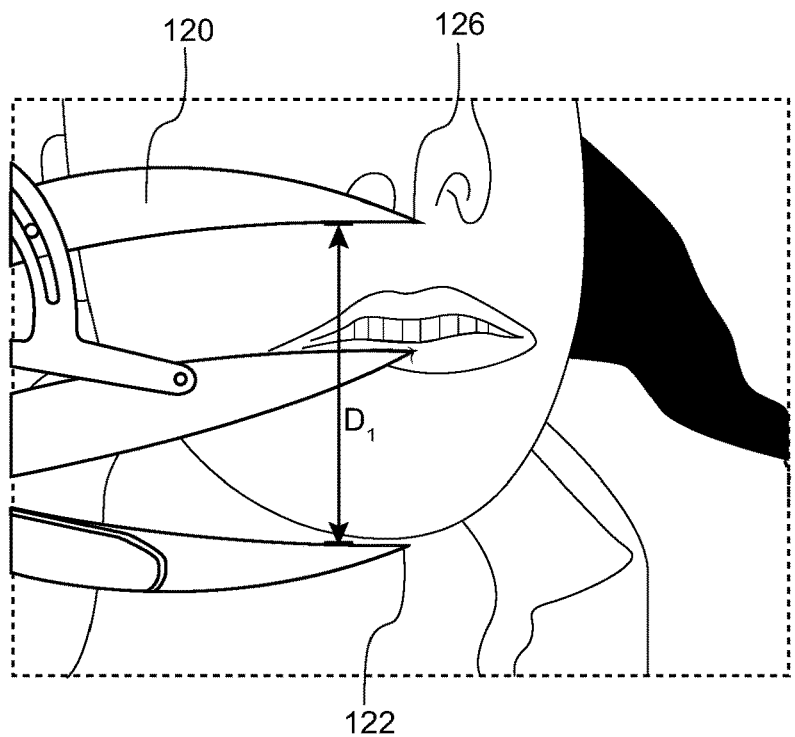
FIG. 9C shows a third step of a method of using the caliper measuring device shown in FIG. 8.

Referring to FIGS. 9A-9C, in one embodiment, the caliper 120 is utilized to measure a first distance between the corner of the patient's eye and the corner of the patient's mouth. The Golden Proportion principle is adhered to when the first distance matches a second distance between the bottom of the patient's nose and the bottom of the patient's chin, as shown in FIG. 9C. The distance $D_1$ between the first and third points 122, 126 in FIG. 9A matches the distance $D_1$ between the first and third points 122, 126 in FIG. 9C. FIG. 9B shows the caliper 120 with the patient's mouth slightly open. After all of a patient's teeth have been removed, it is difficult to replicate this vertical dimension of occlusion to conform to the Golden Proportion principle. The VDO jig disclosed herein is utilized for establishing a desired vertical dimension of occlusion, retaining the vertical dimension of occlusion information, and utilizing the collected information in a laboratory for creating a denture prosthetic. In one embodiment, the VDO jig enables vertical and/or lateral changes in the denture prosthetic to be made so that the final product facilitates comporting with the Golden Proportion principle. The VDO jig enables adjustment in the vertical and lateral direction, as necessary.

In FIG. 9B, the patient's mouth is slightly open and not fully closed. The distance between the bottom of the nose and the bottom of the chin is more than the preferred distance $D_1$. In FIG. 9C, the patient has fully closed her mouth so that the upper and lower teeth are pressed together. The distance between the bottom of the nose and the bottom of the chin matches the preferred distance $D_1$. The VDO jig disclosed herein is designed to retain the preferred vertical dimension of occlusion information and replicate that information when the denture prosthetic devices are created and implanted. Vertical and/or horizontal adjustments may be made to comport with the Golden Proportion principle.

Figure 10:
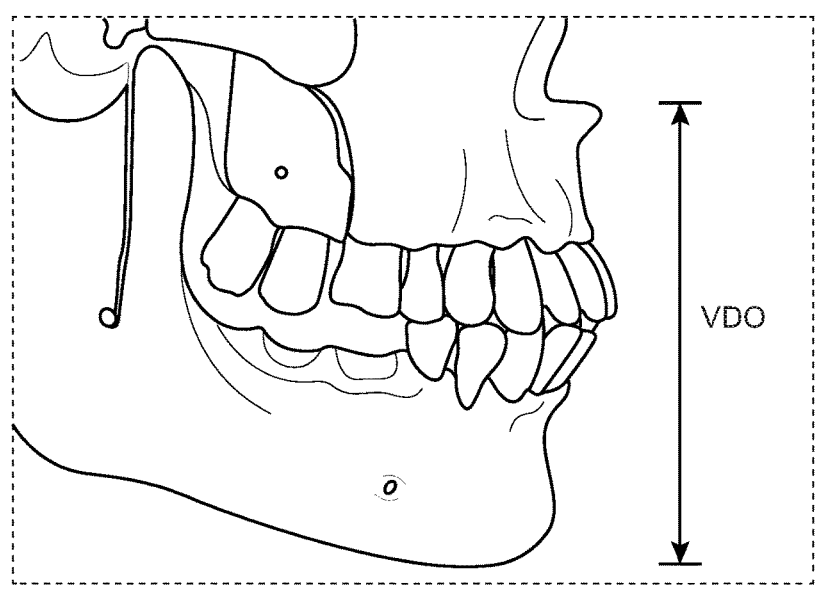
FIG. 10 shows a side view of a human skull including a nasal spine, a maxilla, and a mandible.

Referring to FIG. 10, the vertical dimension of occlusion (VDO) may be measured in a variety of ways. Skeletally, it is the distance between the tip of the nasal spine and the tip of the mentum (chin bone) or the base of the mandible. This distance is designated VDO in FIG. 10. Once this dimension is established, such as by using the contact of the maxillary and mandibular teeth, this relationship between the maxilla and the mandible can be related to other objects that are fixed into position, such as orthodontic brackets attached to natural teeth and/or a temporary anchorage devices (TAD) attached to maxilla or mandible bone.

In the dental arts, the term over jet (OJ) is a measure of the relationship of the position of the mandible and maxilla to one another in the anterior/posterior position. Over jet falls into three different categories. In Class 1, the mandibular cuspids are mesial (forward of) the maxillary cuspids. The buccal cusp (back/outside) of the lower first molar occludes (articulates with) the central fossa of the maxillary first molar. In Class 2, the lower mandibular cuspid is distal (posterior) to the maxillary cuspid. The mesial-buccal cusp of the lower first molar occludes with central fossa of the maxillary first molar. In Class 3, the mandibular incisors are edge to edge or mesial (anterior) to the maxillary incisors. The cusp of the mandibular molars occlude mesial to the central fossa of the maxillary molar.

Stated another way, in Class 1, the upper teeth stick out in front of the lower teeth; in Class 2, the lower teeth are significantly behind the upper teeth; and in Class 3, the lower teeth are edge to edge or forward of the upper teeth. Depending upon the category of over jet, a TAD gantry 30 (FIG. 2) having a particular length be selected. TAD gantries having different lengths are shown and described above in FIGS. 7A-7E. By way of example, a longer TAD gantry is used for Class 2 and a shorter TAD gantry is used for Class 3.

For practical purposes of using the VDO jig disclosed herein, the over jet is the relationship of the orthodontic brackets attached to the natural teeth relative to the temporary anchorage devices (TAD) attached to a jaw bone. If the orthodontic brackets are mesial (in front of) the TAD, then there is a plus over jet. If the orthodontic brackets are distal to (behind) the TAD, then there is a negative over jet. In one embodiment, a dental surgeon will select one of the TAD gantries 30A-30E shown in FIGS. 7A-7E so that the vertical support column 24 (FIG. 1) is parallel to the front line of the patient's face.

The TAD gantry length that is used may also depend upon the angle between the lateral support arms. In one embodiment, the more acute the angle between the lateral support arms 26, 28 (FIG. 1), the longer the TAD gantry 30 (FIG. 1) will have to be. As a result, the orthodontic brackets should be placed in the most facial direction possible to minimize this angle.

Figure 11A:
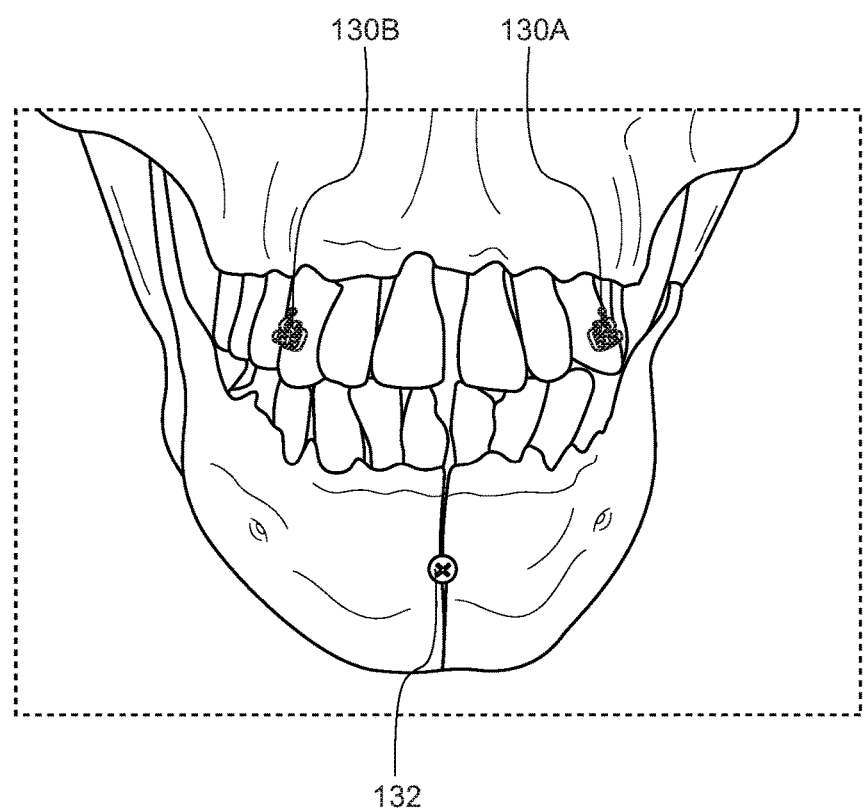
FIG. 11A shows a front view of a patient during an All-On-4 procedure, in accordance with one embodiment of the present invention.

Referring to FIG. 11A, in one embodiment, orthodontic brackets 130A, 130B are affixed on the cuspids of the arch (e.g., the maxilla) on which natural teeth will remain. In one embodiment, the orthodontic brackets 130A, 130B may be bonded onto the teeth. A temporary anchorage device (TAD) 132 is placed at the mid-line of the opposing arch (e.g., the mandible) which will be surgerized. The vertical dimension of occlusion now has an established relationship between the three points that will be recorded and retained by using the VDO jig 20 (FIG. 1). In one embodiment, the orthodontic brackets may be placed on teeth on the mandible and the TAD may be placed at the mid-line of the maxilla.

Figure 11B:
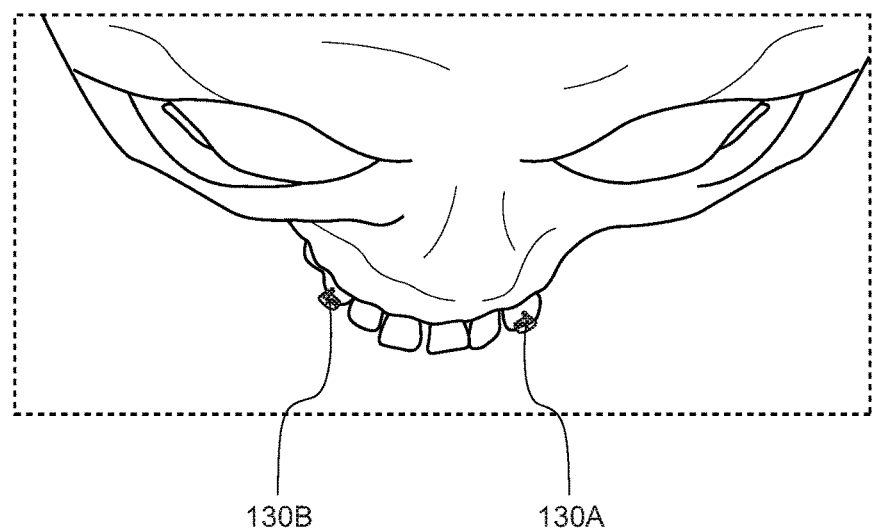
FIG. 11B shows a top view of the patient of FIG. 11A, in accordance with one embodiment of the present invention.

Referring to FIG. 11B, the first and second orthodontic brackets 130A, 130B are secured to the cuspids of the upper arch. The arch curvature and tooth angle are determined by looking at the arch from a vertical position. This angle is estimated and set by recreating that angle using the two lateral support arms 26, 28 (FIG. 1 of the VDO jig), and tightening fasteners or screws to hold the two lateral support arms in place at the angle.

Figure 11C:
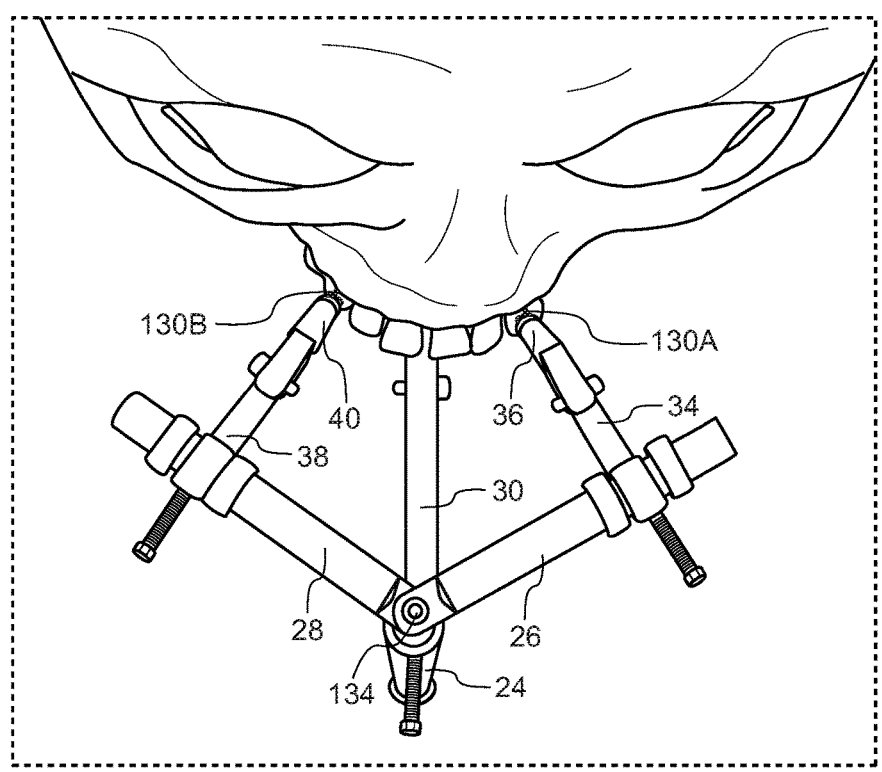
FIG. 11C shows a top perspective view of the VDO jig of FIG. 1 attached to a patient during an All-On-4 procedure, in accordance with one embodiment of the present invention.

Referring to FIG. 11C, in one embodiment, in order to establish an angle that conforms to the arch curvature, the first lateral support arm 26 is swung about the vertical support column 24 until the engagement swivel 36 at the distal end of the first tooth gantry 34 abuts against the opposing first orthodontic bracket 130A affixed to a first cuspid. Similarly, the second lateral support arm 28 is swung about the vertical support column 24 until the engagement swivel 40 at the distal end of the second tooth gantry 38 abuts against the opposing second orthodontic bracket 130B affixed to a second cuspid. The engagement swivel 32 (FIG. 1) at the distal end of the TAD gantry 30 preferably abuts against the TAD 132 shown in FIG. 11A. The length of the shaft of the TAD gantry 30 is preferably selected so that the vertical support column 24 is parallel with the front line of the patient's face. The angle between the first and second lateral support arms 26, 28 preferably matches the angle shown in FIG. 11B. The VDO jig 20 includes a screw 134 that may be tightened for maintaining the angle between the first lateral support arm 26 and the second lateral support arm 28. That information may be registered and utilized later for replication during denture implantation.

A TAD gantry 30 having a particular length is chosen to allow for the existing over jet and the engagement swivel is fastened to the TAD on the mandible with an orthodontic elastic or ligature wire. The appropriate angle to engage the axial inclination of the TAD is chosen and the screw is tightened. The most advantageous vertical position of the TAD gantry is chosen and the gantry screw is tightened into position.

Figure 11D:
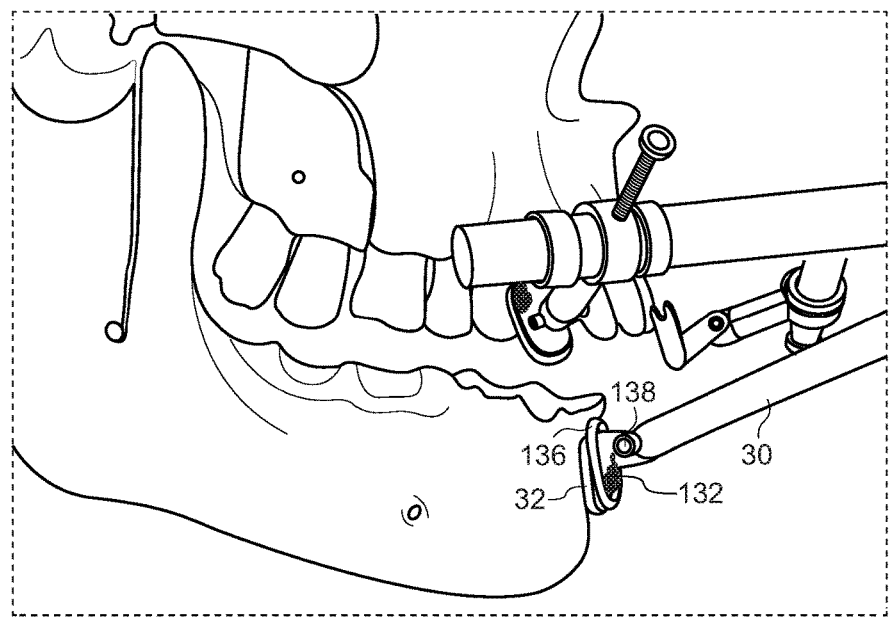
FIG. 11D shows a left side view of the VDO jig of FIG. 11C attached to a patient during an All-On-4 procedure, in accordance with one embodiment of the present invention.

Referring to FIG. 11D, in one embodiment, a TAD gantry 30 having an appropriate length is chosen to accommodate the existing over jet. The engagement swivel 32 is fastened to the TAD 132 utilizing an orthodontic elastic 136. In one embodiment, rather than using an orthodontic elastic, medical personnel may use suture or a ligature wire. An appropriate angle to engage the axial inclination of the TAD 132 is chosen and a gantry screw 138 is tightened. As noted above, the most advantageous vertical position of the TAD gantry 30 is chosen and the gantry screw 138 is tightened into position.

Figure 11E:
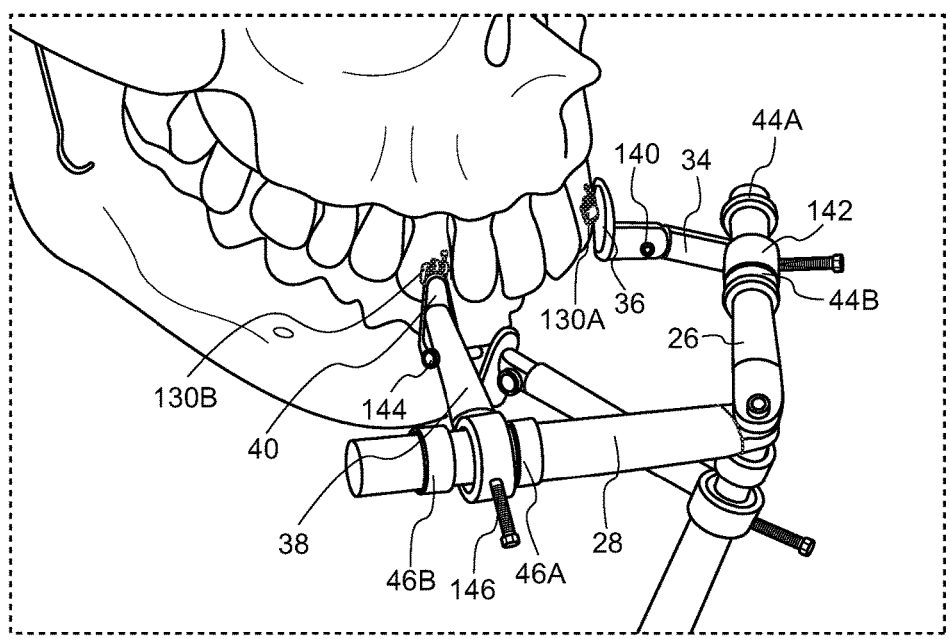
FIG. 11E shows a left side perspective view of the VDO jig of FIG. 11C attached to a patient during an All-On-4 procedure, in accordance with one embodiment of the present invention.
Figure 11F:
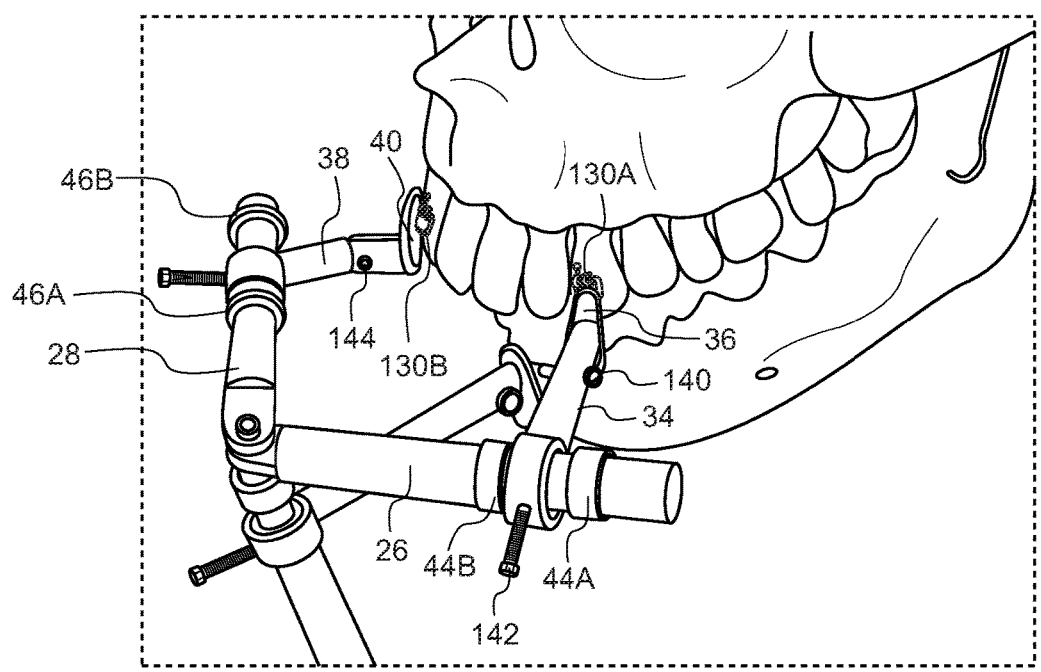
FIG. 11F shows a right side perspective view of the VDO jig of FIG. 1 attached to a patient during an All-On-4 procedure, in accordance with one embodiment of the present invention.

Referring to FIGS. 11E and 11F, in one embodiment, the first and second tooth gantries 34, 36 are moved into optimal position laterally on the respective first and second lateral support arms 26, 28 so that the engagement swivels 36, 40 at the distal ends of the tooth gantries engage the orthodontic brackets 130A, 130B. The tooth gantries 130, 136 are swung or rotated about the respective first and second lateral support arms 26, 28 until the engagement swivels contact the opposing orthodontic brackets 130A, 130B.

After all the teeth in the surgical arch (e.g., the mandible) are removed and the alveolar crest is eliminated, the VDO of the patient may be accurately reproduced by reintroducing and fastening the VDO jig to its original positions on the fixed points which were previously established by the orthodontic brackets and the TAD. Using the previously established three fixed points will allow for extremely accurate conversion of the denture, which has been specifically crafted for the patient. It will also allow for fast and easy modification of the temporary tubular abutments (in terms of length) prior to the introduction of the implant transfer guide, which has been previously custom manufactured for this purpose.

In one embodiment, the engagement swivels 36, 40 at the distal ends of the tooth gantries are adjusted to an appropriate axial inclination and the engagement swivel screws 140, 142 are tightened to maintain the angle(s). The first engagement swivel 36 is fastened to the first orthodontic bracket 130A using orthodontic elastic or ligature wire. A tooth gantry screw 144 is tightened to hold the position of the first tooth gantry 34 relative to the first lateral support arm 26. The second engagement swivel 40 is fastened to the second orthodontic bracket 130B using orthodontic elastic or ligature wire and the second tooth gantry screw 142 is tightened for establishing the position of the second tooth gantry 36 relative to the second lateral support arm 28. The alignment markers 44A, 44B are moved into position to further document the position of the first tooth gantry 34 along the length of the first lateral support arm 26, and the alignment markers 46A, 46B are moved into place on the second lateral support arm 28 to further document the position of the second tooth gantry 38 relative to the length of the second lateral support arm 28. Thus, the VDO jig 20 may be utilized for establishing the vertical dimension of occlusion, the arch curvature, and the angles of the teeth, and this information can be recorded for use during the surgery. After the above-noted information has been recorded and retained, the VDO jig may be removed for performing the surgical procedure.

Figure 12:
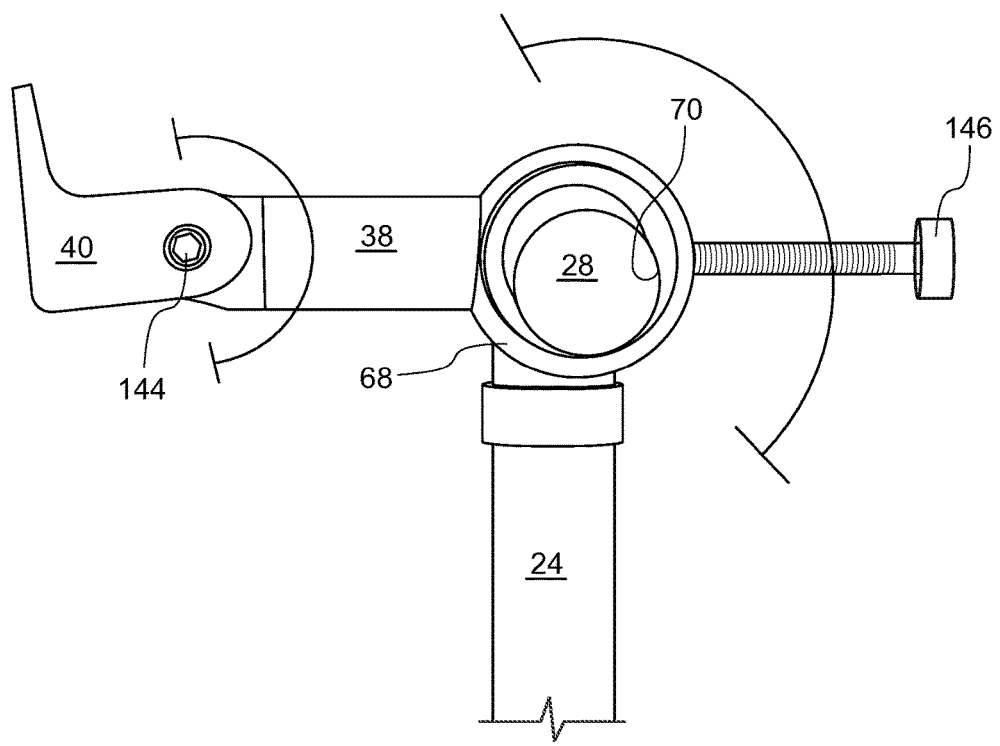
FIG. 12 shows the rotation of a tooth gantry relative to a lateral support arm of a VDO jig and the rotation of an engagement swivel at a distal end of the tooth gantry, in accordance with one embodiment of the present invention.

Referring to FIG. 12, in one embodiment, the second lateral support arm 28 is attached to the vertical support column 24 so that the distal end of the second lateral support arm 28 may swing about the upper end of the vertical support column 24. The second tooth gantry 38 is coupled with the second lateral support arm 28. The second tooth gantry 28 includes a ring 68 having a central opening 70 that slides over the second lateral support arm 28. The ring 68 enables the second tooth gantry 38 to swing about the second lateral support arm 28. The tooth gantry 38 also has a distal end and the engagement swivel 40 is pivotally connected with the distal end. The angle of the engagement swivel 40 relative to the distal end of the tooth gantry 38 may be adjusted. An engagement swivel screw 144 may be tightened for setting the angle of inclination of the engagement swivel 40 relative to the shaft of the tooth gantry 38.

Figure 13:
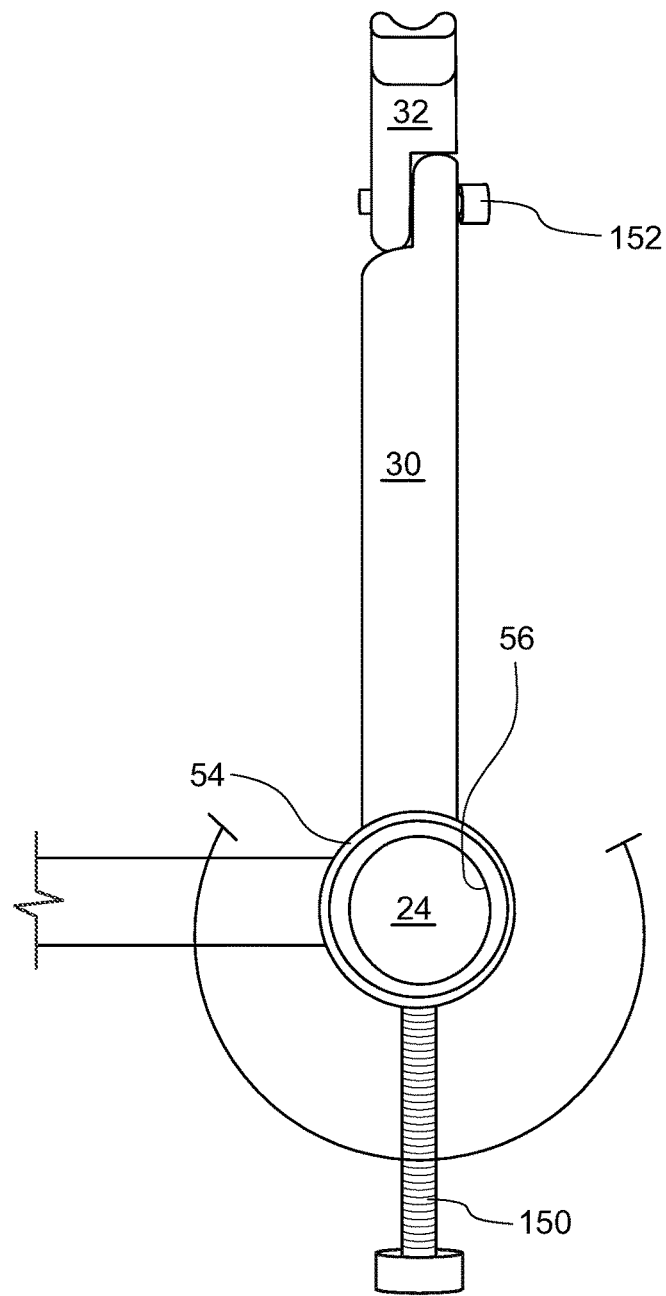
FIG. 13 shows rotation of a TAD gantry relative to a vertical support column of a VDO jig and an engagement swivel pivotally connected with a distal end of the TAD gantry, in accordance with one embodiment of the present invention.

FIG. 13 shows how the TAD gantry 30 may swing about the vertical support column 24. The TAD gantry 30 has a ring 54 with a central opening 56 that enables the ring to slide over the vertical support column 24. The TAD gantry 30 may swing about the vertical support column 24 and slide up and down in a vertical direction relative to the vertical support column 24. When a position for the TAD gantry has been attained, the TAD gantry screw 150 may be tightened for holding that position.

FIG. 13 also shows engagement swivel 32 pivotally connected with a distal end of the TAD gantry 30. When a desired angulation of the engagement swivel 32 relative to the distal end of the TAD gantry 30 has been attained, an engagement swivel tightening screw 152 may be tightened for affixing the angle of the engagement swivel 32 relative to the TAD gantry 30.

Figure 14:
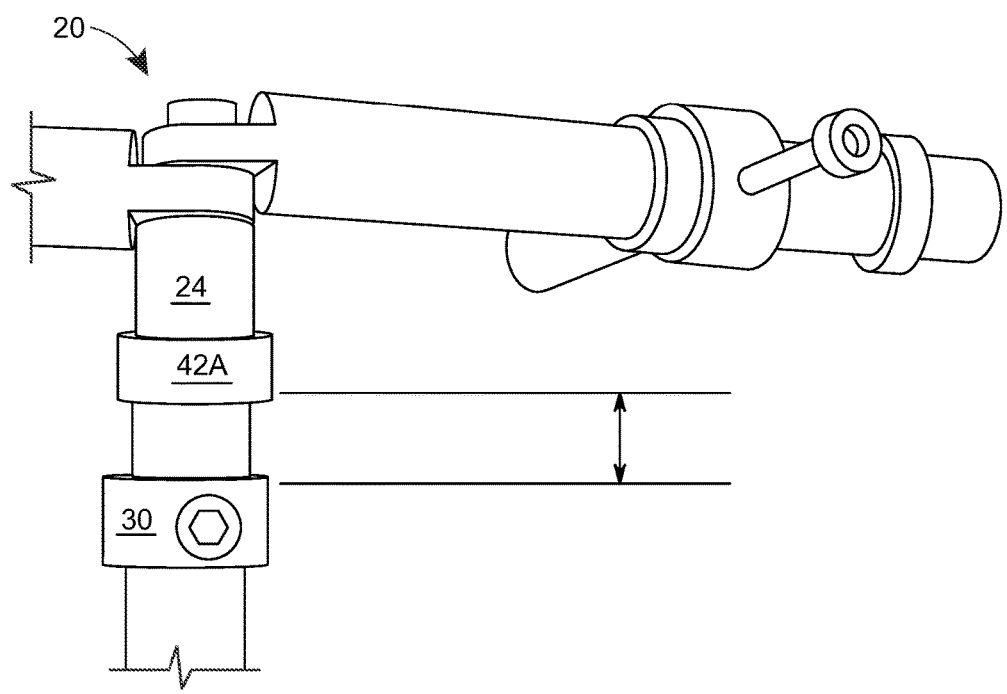
FIG. 14 shows a front elevation view of a vertical support column and two lateral support arms of the VDO jig of FIG. 1, in accordance with one embodiment of the present invention.

Referring to FIG. 14, once the vertical dimension of occlusion is established using the VDO jig 20, it can be adjusted to emulate any adjustment made by the laboratory during the fabrication of the denture appliance and be converted at the time of the surgery. In one embodiment, the TAD gantry 30 is moved down the vertical support column 24 by a distance that is equal to that of a pin on a laboratory articulator. The alignment marker 42A may be used for making the adjustment. In FIG. 14, the TAD gantry is moved from the alignment marker 42A by a distance that is equal to the distance of the articulator pin. In one embodiment, adjustments may be made to improve the final VDO and conform to the Golden Proportion.

Figure 15:
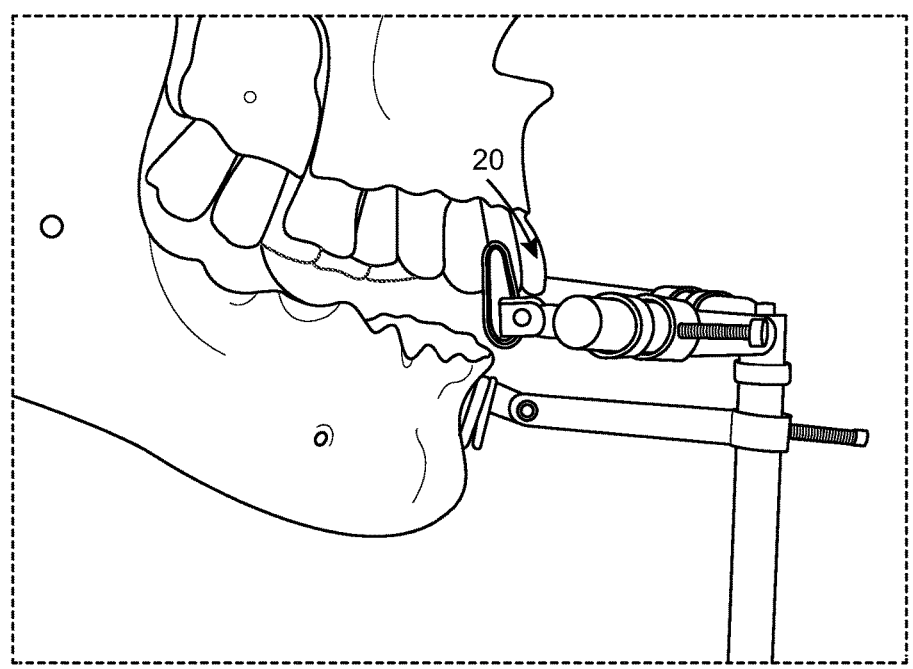
FIG. 15 shows a method of conducting a surgical procedure using the VDO jig of FIG. 1, in accordance with one embodiment of the present invention.

Referring to FIG. 15, after all of the teeth in the lower surgical arch have been removed and the alveolar crest has been eliminated, the vertical dimension of occlusion of the patient may now be accurately reproduced by reintroducing and fastening the VDO jig to the original positions on the fixed points (e.g., the two orthodontic brackets affixed to the cuspids and the TAD affixed to the mandible). The use of the VDO jig enables extremely accurate placement of the prefabricated denture prosthetic. The use of the VDO jig also enables fast and easy modification of the temporary tubular abutments (in terms of length) prior to the introduction of a pre-made implant transfer guide.

Figure 16:
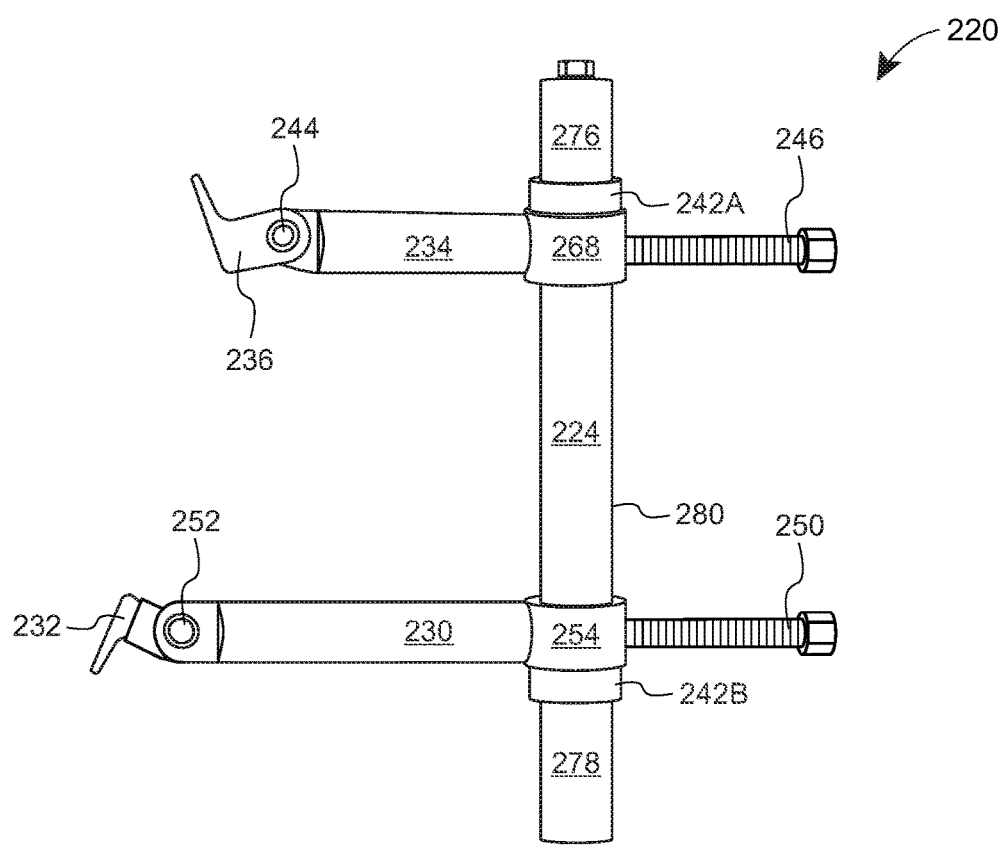
FIG. 16 shows a VDO jig used for conducting an All-On-4 surgical procedure, in accordance with one embodiment of the present invention.

Referring to FIG. 16, in one embodiment, a VDO jig 220 may have only two fixed points for recording the vertical dimension of occlusion for a patient. In one embodiment, the VDO jig 220 has a vertical support column 224 having a shaft 280 with an upper end 276 and a lower end 278. A first TAD gantry 234 is coupled with the vertical support column 224 adjacent the upper end 276 of the shaft 280. The first TAD gantry 234 has a ring 268 at the proximal end that slides over the shaft 280 of the vertical support column, and a distal end coupled with an engagement swivel 236. A first alignment ring 242A may be used to confirm the position of the ring 268 of the first TAD gantry 234 on the shaft 280 of the vertical support column 224. The engagement swivel 236 is adapted to pivot to match the angle of inclination of a tooth contacted by the engagement swivel.

In one embodiment, the VDO jig 220 also includes a second TAD gantry 230 having a proximal end with a ring 254 that slides over the vertical support column 224. The second TAD gantry 230 may be located adjacent the lower end 278 of the vertical support column 224. An engagement swivel 232 is pivotally connected with the distal end of the second TAD gantry 230. The engagement swivel is adapted to be temporarily affixed to a TAD secured to bone (e.g., the mandible). A second alignment ring 242B may be used to confirm the position of the ring 254 of the second TAD gantry 230 on the shaft 280 of the vertical support column 224. The engagement swivel 232 is adapted to pivot to match the angle of inclination of the opposing bone contacted by the engagement swivel.

The VDO jig has fasteners or locking screws for setting the positions of the first TAD gantry 234, the engagement swivel 236 at the distal end of the first TAD gantry 234, the second TAD gantry 230, and the engagement swivel 232 at the distal end of the second TAD gantry 230. In one embodiment, the first TAD gantry 234 is adapted to swing about the upper end of the vertical support column 224. The first TAD gantry 234 may also slide up and down the length of the vertical support column 224. The position of the first TAD gantry relative to the vertical support column may be set by a locking screw 246. The angle of inclination of the engagement swivel 236 relative to the distal end of the first TAD gantry 234 may be established and locked in place by locking screw 244.

In one embodiment, the second TAD gantry 230 is adapted to swing about the lower end of the vertical support column 224. The second TAD gantry 230 may also slide up and down the length of the vertical support column 224. The position of the second TAD gantry relative to the vertical support column may be set by tightening a locking screw 250. The angle of inclination of the engagement swivel 232 relative to the distal end of the second TAD gantry 230 may be established and locked in place by tightening a locking screw 252.

Figure 17:
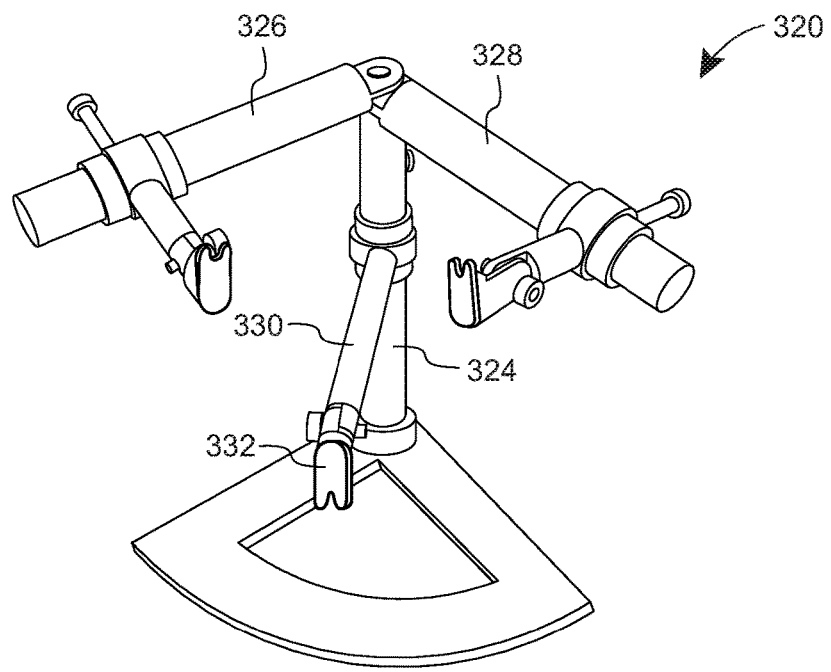
FIG. 17 shows a perspective view of a vertical dimension of occlusion (VDO) jig including a vertical support column, first and second lateral support arms, a temporary anchorage device (TAD) gantry, first and second tooth gantries, and three engagement swivels, in accordance with one embodiment of the present invention.

Referring to FIG. 17, in one embodiment, a VDO jig 320 is made of stainless steel, which is more rugged than polymer materials, and which may be easily sterilized between surgical procedures. In one embodiment, the Vertical support column 324, the first and second lateral support arms 326 and 328, and the TAD gantry 330 may be hollow to minimize the weight of the VDO jig 320. In other embodiments, the VDO jig 320 may also be made of biocompatible metals, biocompatible alloys, and polymers such as surgical steel, titanium, and aluminum.

Figure 18:
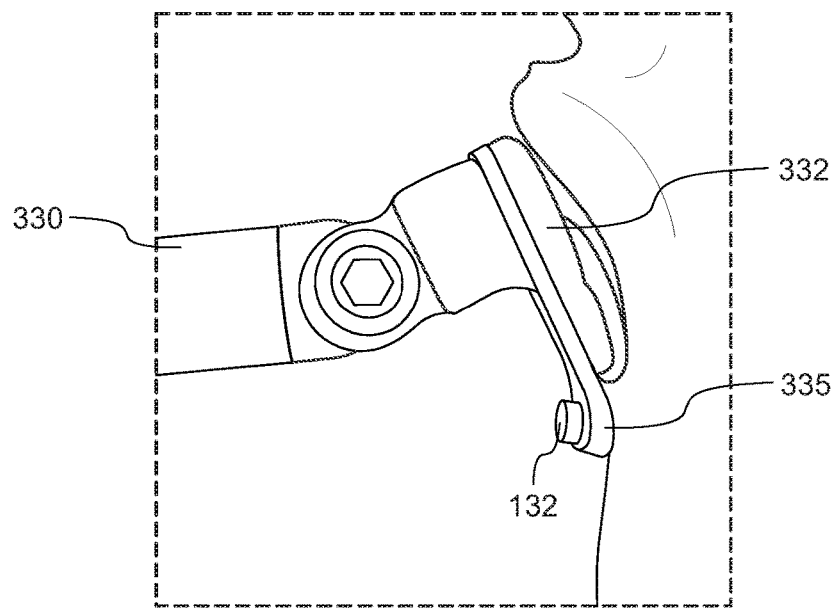
FIG. 18 shows a side view of a TAD gantry, in accordance with one embodiment of the invention.

Referring to FIGS. 17 and 18, in one embodiment, the TAD gantry 330 of the VDO jig 320 preferably includes an engagement swivel 332 coupled with the free end of the TAD gantry 330. A securing element, such as an orthodontic elastic, may be used for securing the engagement swivel 332 with a temporary anchoring device 132 inserted into a patient's mandible.

In one embodiment, a metal VDO jig may, due to its own weight, pull away from a tooth and/or a temporary anchoring device because orthodontic elastics may not be strong enough to hold the VDO jig in place.

Figure 19:
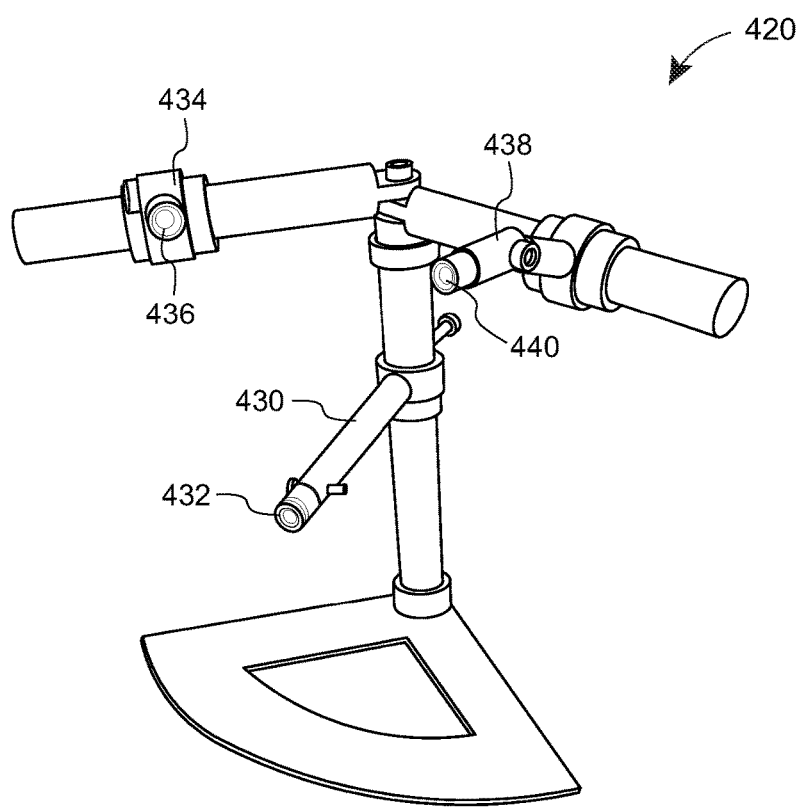
FIG. 19 shows a perspective view of a vertical dimension of occlusion (VDO) jig including a vertical support column, first and second lateral support arms, a temporary anchorage device (TAD) gantry, first and second tooth gantries, and three engagement sockets, in accordance with one embodiment of the present invention.

Referring to FIG. 19, in one embodiment, a VDO jig 420 preferably has one or more ball and socket components secured to the free ends of first and second tooth gantries 434 and 438, and the free end of a TAD gantry 430. The ball and socket components desirably provide for a stronger connection between the VDO jig and the maxilla and mandible of a patient, particularly for a VDO jig made out of heavier metal materials. In one embodiment, a TAD gantry socket 432 is secured to the free end of the TAD Gantry, a first tooth socket 436 is secured to the free end of the first tooth gantry 434 and a second tooth socket 440 is secured to the free end of the second tooth gantry 438.

Figure 20:
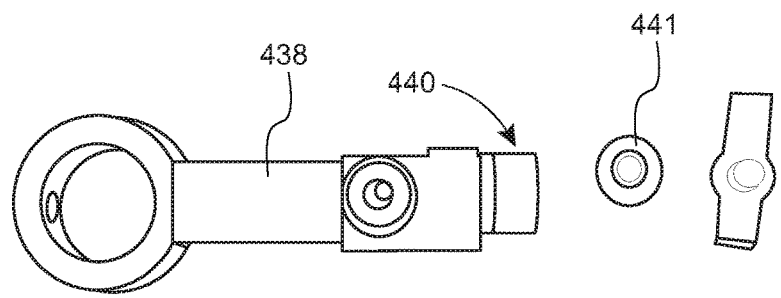
FIG. 20 shows a side view of a tooth gantry, in accordance with one embodiment of the invention.
Figure 21:
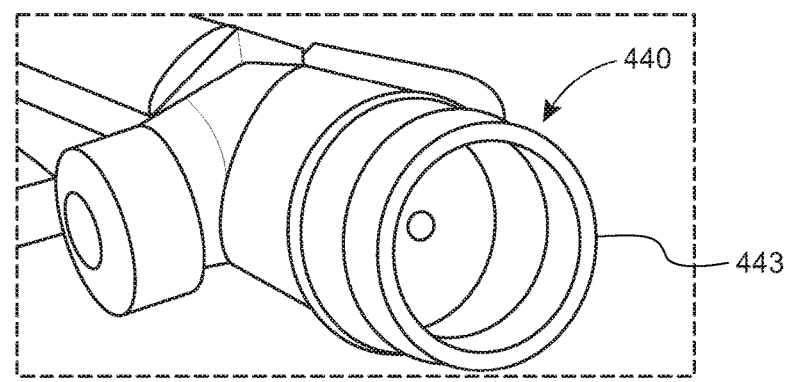
FIG. 21 shows a free end of the tooth gantry of FIG. 20.

Referring to FIGS. 20 and 21, in one embodiment, a ball and socket component 440 at the free end of a gantry 438 preferably includes a nylon female insert that is inserted into an open end of a collar 443, such as a metal collar. In one embodiment, the collar 443 is free to pivot and/or rotate relative to the free end of the gantry 438.

Figure 22:
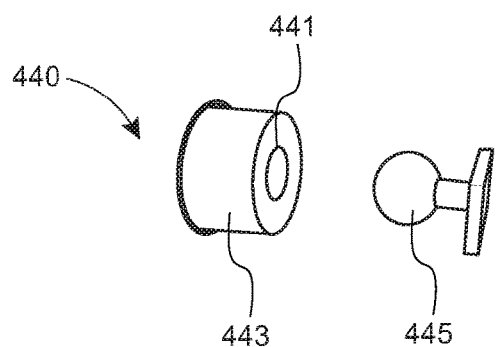
FIG. 22 shows a ball and socket structure for a VDO jig, in accordance with one embodiment of the present patent application.
Figure 23A:
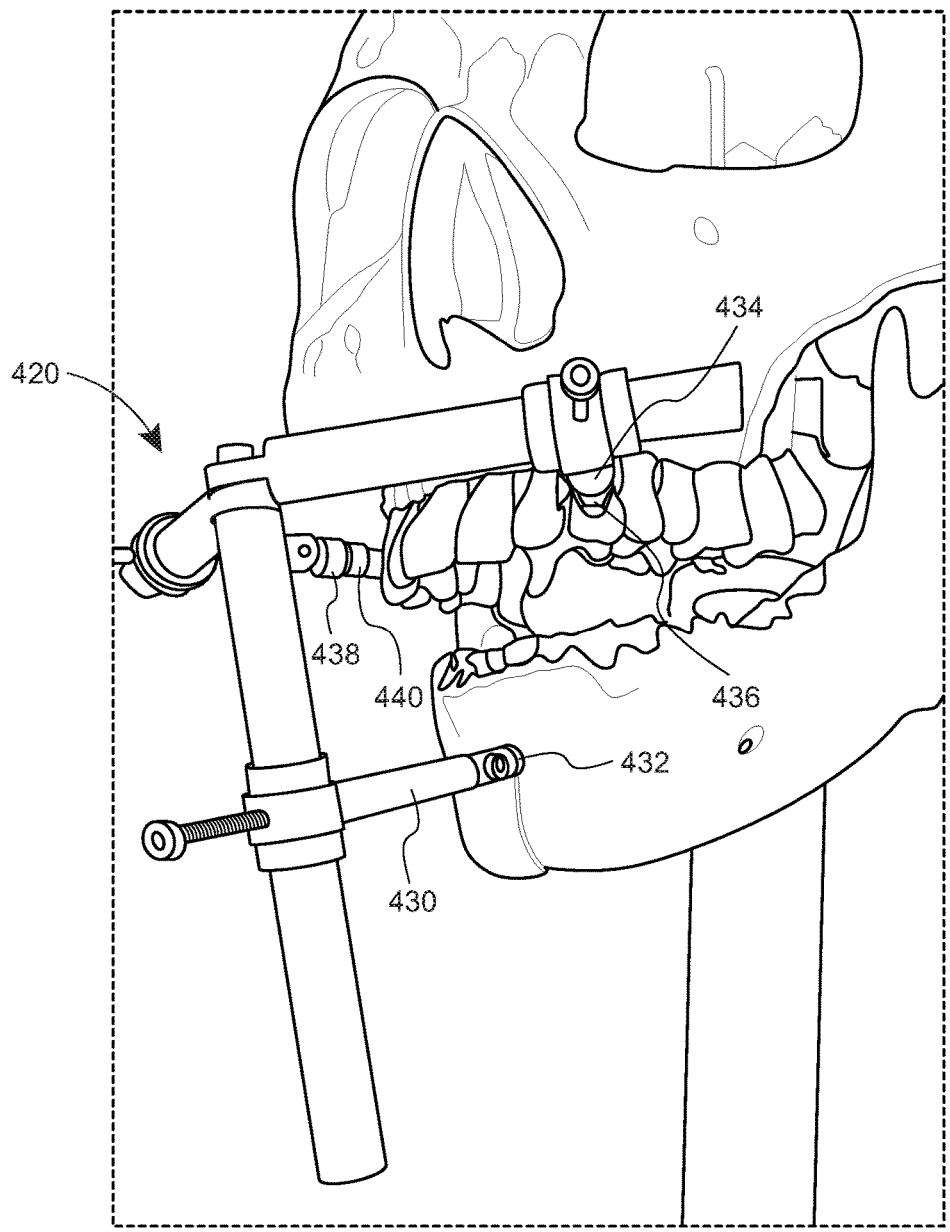
FIG. 23A shows a right side perspective view of the VDO jig of FIG. 19 secured to a patient, in accordance with one embodiment of the present invention.
Figure 23B:
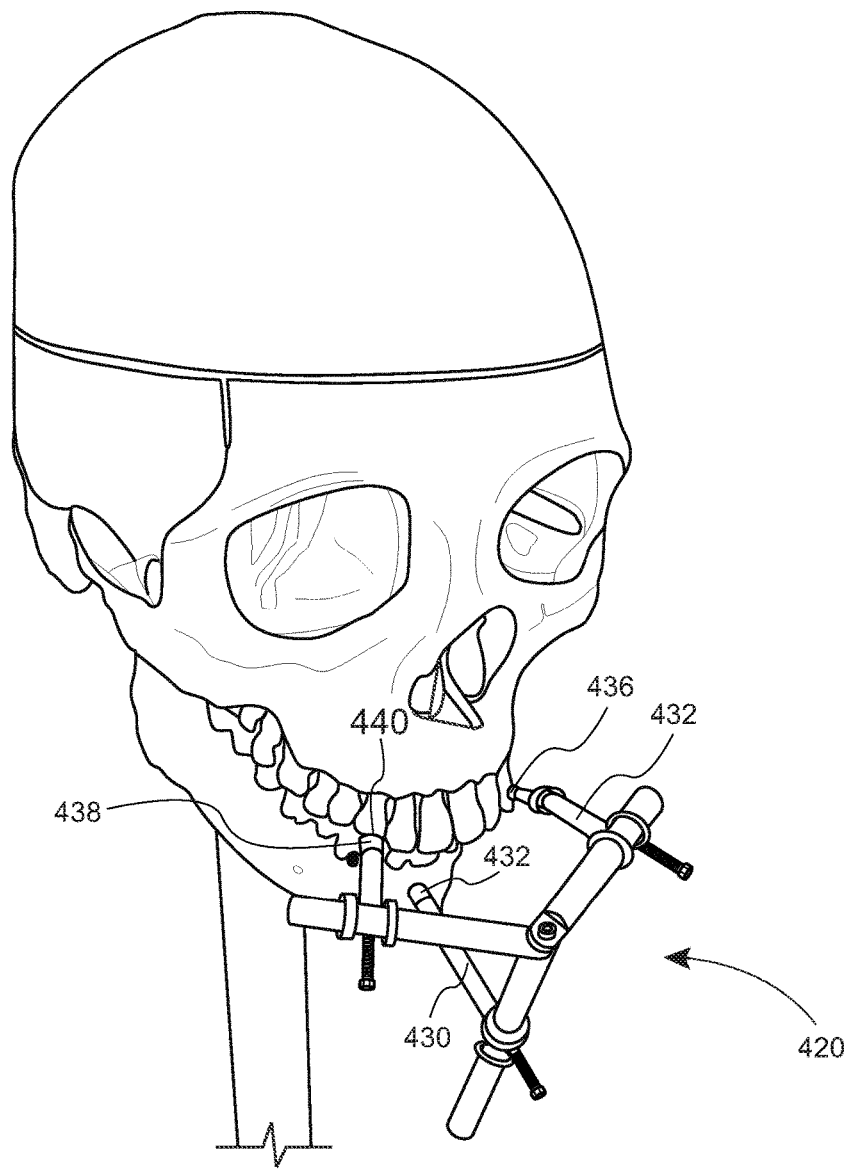
FIG. 23B shows a top perspective view of the VDO jig of FIG. 19 secured to a patient, in accordance with one embodiment of the present invention.
Figure 23C:
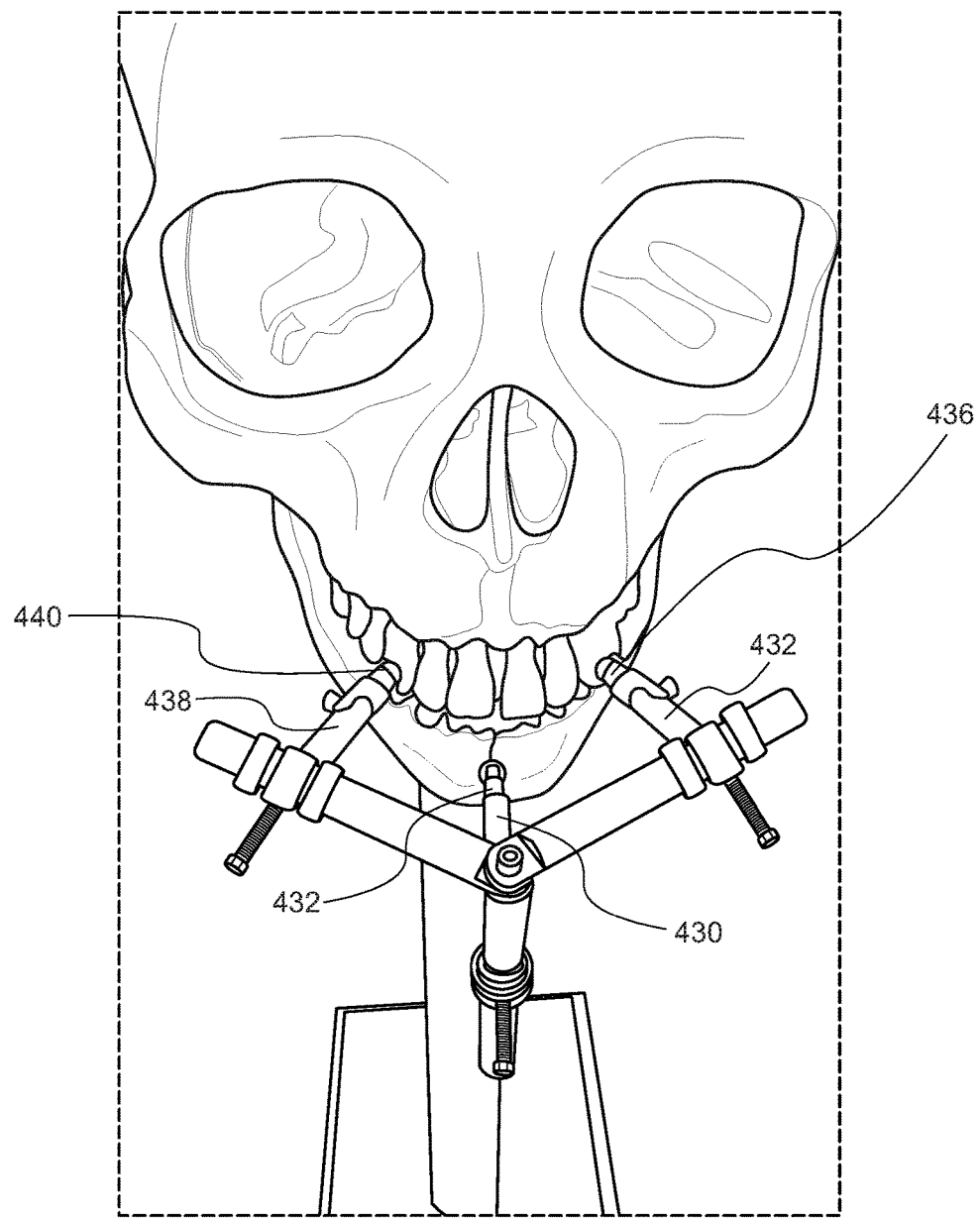
FIG. 23C shows a front perspective view of the VDO jig of FIG. 19 secured to a patient, in accordance with one embodiment of the present invention.
Figure 23D:
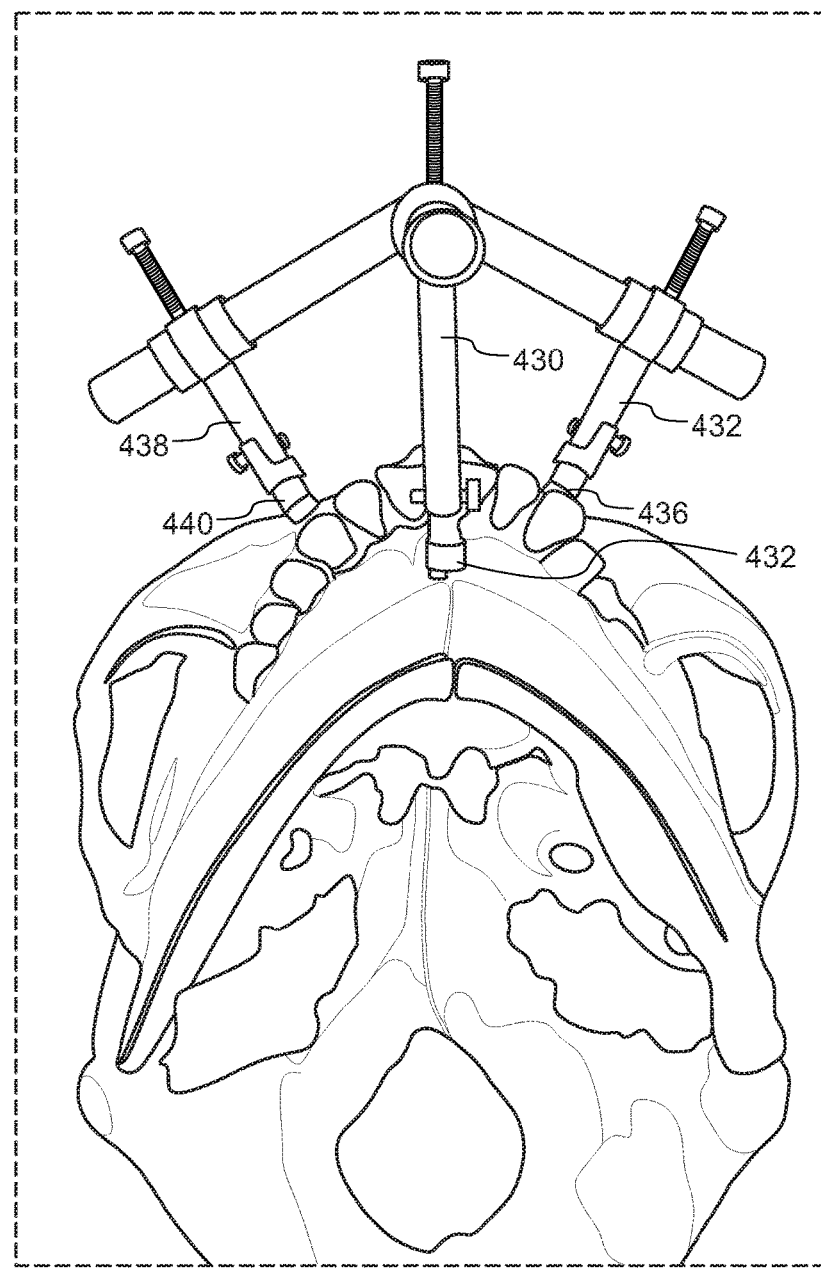

Referring to FIG. 22, in one embodiment, the ball and socket component 440 preferably includes a ball 445 that is attached to bone or teeth, such as by using an adhesive. After the ball 445 is secured a tooth or bone, the ball 445 may be pressed into the nylon female inert 441 of the collar 443 for securing the gantry 438 (FIG. 21A) to a tooth or bone. In one embodiment, the use of the ball and socket components shown in FIGS. 20-22 makes it easier to secure the VDO jig in place relative to the maxilla and the mandible of a patient, and also makes it easier to decouple the VDO jig from being secured with the maxilla and the mandible of a patient. In one embodiment, the ball and socket component is similar to those sold by Zimmer-Biomet Corp.

Referring to FIGS. 23A-23D, in one embodiment, the VDO jig 420 of FIGS. 20-22 may be secured to the maxilla and the mandible of a patient. In one embodiment, the free end of a first tooth gantry 434 is secured to a first tooth using a first socket 436 that is snap fit onto a ball component secured to the first tooth, the free end of a second tooth gantry 438 is secured to a second tooth using a second socket 440 that is snap fit onto a ball component secured to the second tooth, and the free end of a TAD tooth gantry 430 is secured to a mandible using a TAD gantry socket 432 that is snap fit onto a ball component secured to the mandible.

In one embodiment, a ball component is preferably fastened to teeth of an arch (e.g., cuspid teeth) or bone (e.g., mandible bone), such as by using an adhesive. Other securing methodologies may be used such as welding (laser, spot, or other). In one embodiment, a metal collar with a female nylon insert inside the metal collar will engage the ball fastened to the teeth and/or bone. The ball and socket arrangement is desirably simpler, cleaner and easier to use and allows for high precision.

In one embodiment, a VDO jig has thumb screws that may be utilized for coupling the VDO jig components together and holding the jig components in a set position relative to one another after the VDO jig has been properly oriented and configured.

In one embodiment, the metal collar of the ball and socket arrangement is able to rotate and pivot relative to the free ends of the tooth gantries and the TAD gantries to accommodate various attachment configurations such as a straight-on attachment configuration as well as a 90 degree attachment for engagement of a vertically placed TAD for a missing cuspid tooth.

Figure 24A:
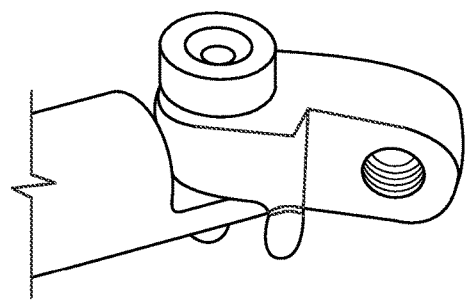
FIG. 24A shows a tooth gantry having a universal joint, in accordance with one embodiment.
Figure 24B:
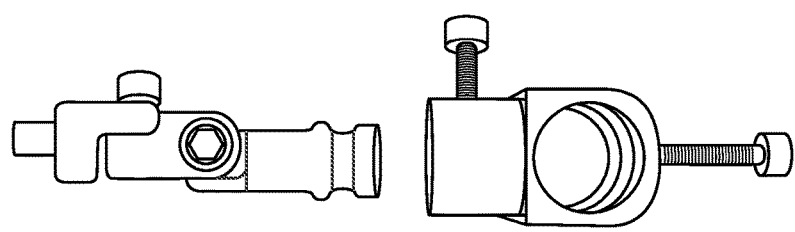
FIG. 24B shows a tooth gantry having a universal joint, in accordance with one embodiment.
Figure 24C:
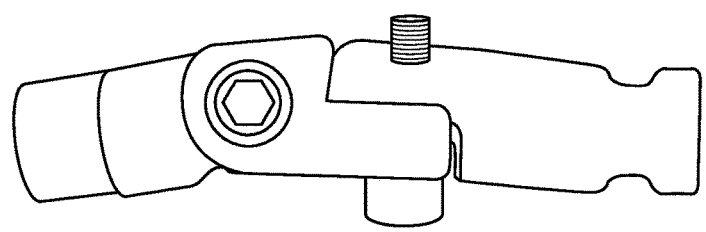
FIG. 24C shows a tooth gantry having a universal joint, in accordance with one embodiment.

Referring to FIGS. 24A-24C, in one embodiment, attaching to the ball component may have to be accomplished at many different angles depending upon the orientation of ball component attached to a tooth and the position of the TAD attached to the mandible. In one embodiment, a universal joint is provided between the free ends of the gantries and the engagement swivel or metal collar of the socket. In one embodiment, the universal joint allows a gantry to act much like the drive shaft in an automobile so that the attachment end of the engagement swivel may be easily placed at any angle and inclination for easy engagement of the ball component.

Figure 25:
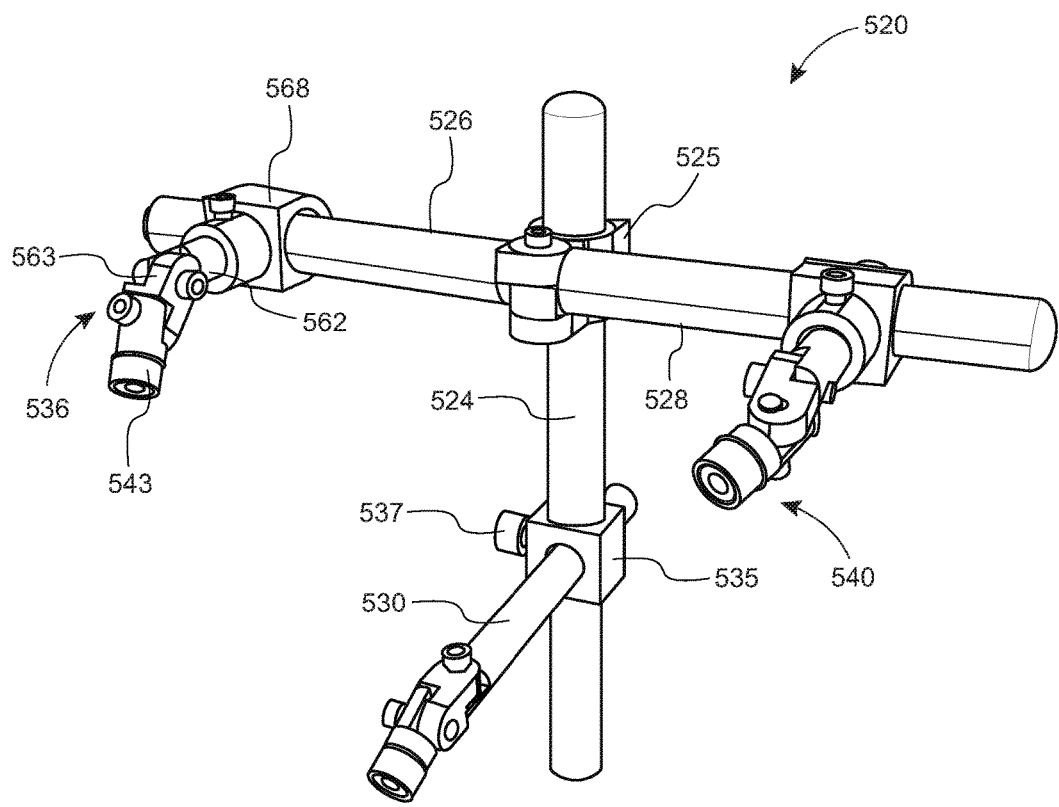
FIG. 25 shows a perspective view of a vertical dimension of occlusion (VDO) jig, in accordance with one embodiment.

Referring to FIG. 25, in one embodiment, a VDO jig 520 preferably includes a vertical support column 524, a first lateral support arm 526 and a second lateral support arm 528. The VDO jig 520 preferably includes a support base 525 for the first and second lateral support arms 526, 528. The support base 525 is able to slide up and down along the length of the vertical support column 524 for making vertical adjustments. In one embodiment, the support base 525 is configured to rotate relative to the vertical support column 524 to make rotation adjustments. After vertical and/or rotation adjustments have been made to the support bas 525, fasteners (e.g., thumb screws) may be tightened to hold the position of the support base.

In one embodiment, the VDO jig 520 desirably includes a TAD gantry support 535 that enables the TAD gantry 530 to slide toward and away from the mandible of a patient. In one embodiment, after the TAD gantry has been slid into a desired position, a thumb screw 537 may be tightened to hold the position of the TAD gantry 530. The TAD gantry support may also be rotatable relative to the vertical support column and may be locked in place after being rotated to a desired position.

Figure 26:
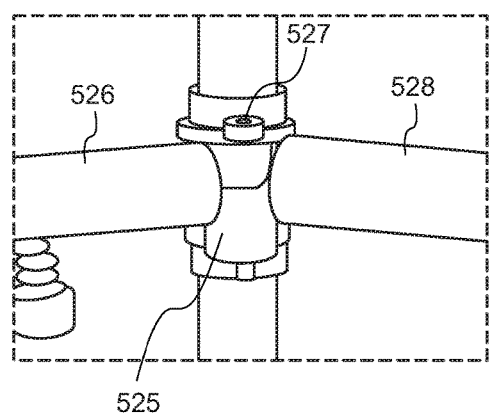
FIG. 26 shows a support base for securing laterally extending support arms to a vertical column, in accordance with one embodiment.

Referring to FIG. 26, in one embodiment, the first and second lateral support arms 526, 528 are pivotally secured to the support base 525 so that the first and second lateral support arms may be placed at different angles relative to one another. One or more fasteners 527 may be used to hold the angular position of the first and second lateral support arms 526, 528 relative to one another.

Figure 27:
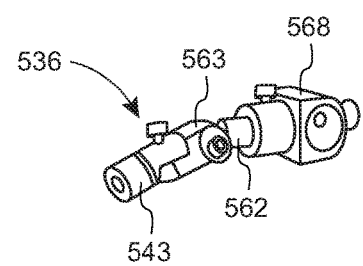
FIG. 27 shows a tooth gantry having a universal joint and a socket, in accordance with one embodiment.

Referring to FIGS. 25 and 27, in one embodiment, a VDO jig 520 preferably includes a tooth gantry system having a tooth gantry swivel base 568, a tooth gantry extension 562, a universal swivel 563, and an engagement swivel 536 having a collar 543, such as a metal collar. The tooth gantry base 568 is adapted to slide along the length of a lateral support arm and is rotatable about the lateral support arm. The tooth gantry base has a fastener that may be engaged for locking the tooth gantry base 568 in place for preventing sliding and rotating the tooth gantry base relative to the lateral support arm. The tooth gantry extension 562 is adapted to slide and/or rotate relative to the tooth gantry base 568 so that the tooth gantry extension 562 may be extended, retracted, and rotated relative to the tooth gantry base 568. A threaded fastener, such as a thumb screw, may be tightened for locking the extended/retracted position of the tooth gantry extension 562 relative to the tooth gantry base 568.

Referring to FIG. 27, the engagement swivel is coupled with the tooth gantry extension 562 via a universal joint that enables the collar 543 to rotate about the longitudinal axis of the tooth gantry extension 562 and pivot relative to the distal end of the tooth gantry extension.

In one embodiment, a ball component is preferably inserted into the collar 543 for securing the free end of the tooth gantry to a ball component anchored to a tooth (e.g., cuspid) or bone. In one embodiment, the ball and socket arrangement is similar to that sold under the name CAB-CAN system by Zimmer-Biomet. In one embodiment, the ball component may be secured to teeth using an adhesive such as a cyanoacrylate adhesive.

Referring to FIG. 28, in one embodiment, the support base 525 for the first and second lateral support arms is configured to slide up and down along the length of the vertical support column 524 (along the axis designated $A_1$) for making vertical adjustments. The support base 525 is also rotatable relative to the vertical support column 524 to make rotation adjustments. After vertical and rotation adjustments have been made to the support base 525, fasteners (e.g., thumb screws) may be tightened to hold the position of the support base 525.

In one embodiment, the VDO jig 520 desirably includes the TAD gantry support 535 that enables the TAD gantry 530 to slide toward and away from the mandible of a patient along the axis designed $A_2$. In one embodiment, after the TAD gantry has been moved into a desired position, a thumb screw 537 may be tightened to hold the position of the TAD gantry 530. In one embodiment, the TAD gantry 530 is rotatable relative to the TAD gantry support 535. A thumb screw or similar component may be tightened to hold the TAD gantry in place and prevent further rotation of the TAD gantry relative to the TAD gantry support.

Referring to FIG. 29, in one embodiment, the first and second lateral support arms 526, 528 are pivotally secured to the support base 525 so that the first and second lateral support arms may be placed at different angles relative to one another. One or more fasteners 527 may be used to hold the angular position of the first and second lateral support arms 526, 528 relative to one another. The tooth gantry extensions 534, 538 may be extended and retracted relative to the respective tooth gantry bases 568, 569. Thumb screws or similar fastening devices may be tightened once the tooth gantry extensions 534, 538 are extended, retracted and/or rotated into a desired position relative to the tooth gantry bases 568, 569.

In one embodiment, the tooth sockets 536, 540 are coupled to the distal ends of the tooth gantry extensions 534, 538 via universal joints that enable the tooth sockets to rotate and pivot relative to the distal ends of the tooth gantry extensions.

Referring to FIG. 30, in one embodiment, a VDO jig 620 includes first and second lateral support arms 626, 628 that extend along a common axis $A_3$, and that are able to slide up and down and rotate relative to a vertical support column 624 via a support base 625. In one embodiment, the first and second lateral support arms 626, 628 do not pivot relative to the support base 625. The VDO jig 620 preferably includes a TAD gantry support 635 that enables the TAG gantry 630 to slide toward and away from the mandible of a patient for adjusting the orientation of the vertical support column relative to the mandible. The structure enables vertical and horizontal adjustments to be made to the tooth gantries and in and out adjustments to be made to the TAD gantry.

Figure 31:
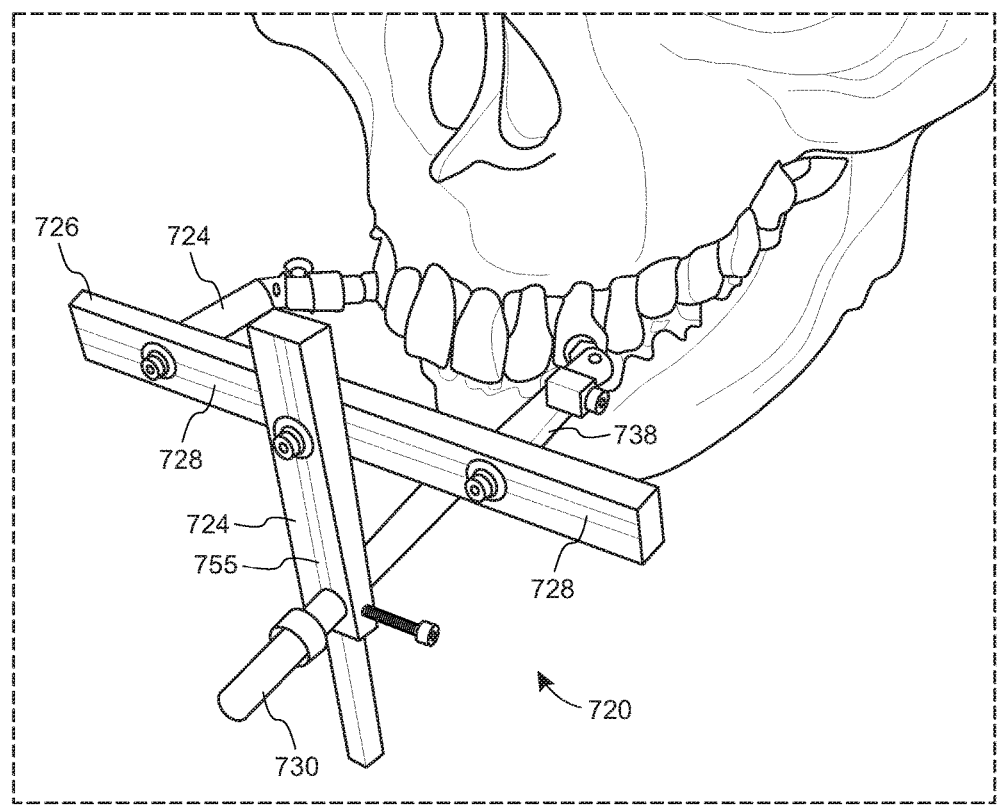
FIG. 31 shows a perspective view of a vertical dimension of occlusion (VDO) jig, in accordance with still another embodiment.
Figure 32:
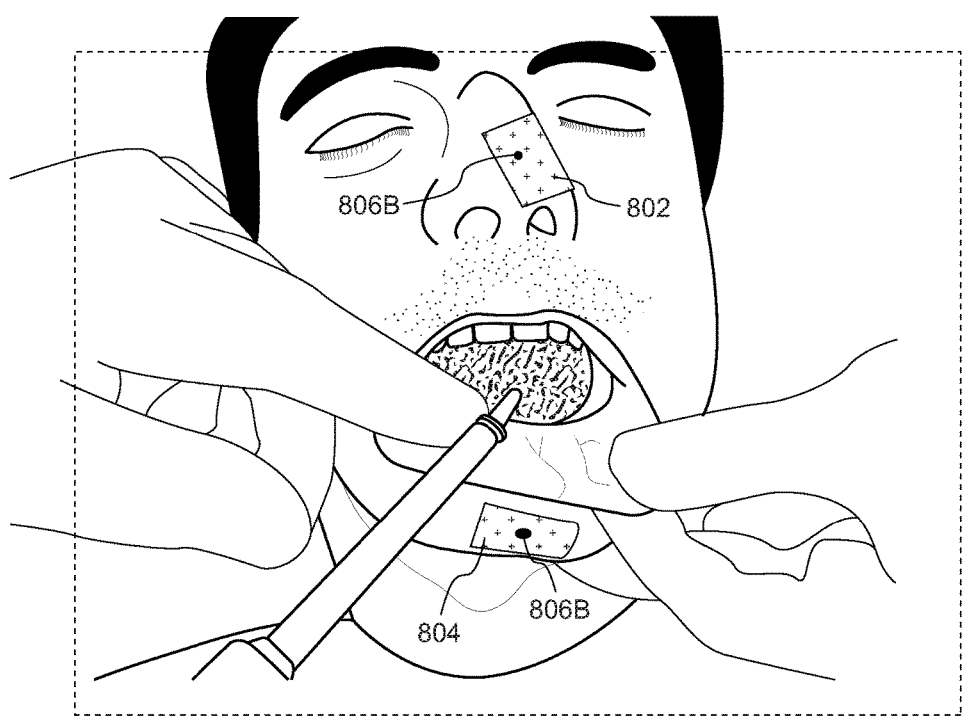
FIG. 32 shows a conventional method of determining a vertical dimension of occlusion of a patient using stickers with dots that are affixed to the patient's nose and chin.

Referring to FIG. 31, in one embodiment, a VDO jig 720 includes a horizontally extending plate 726 having a horizontally extending slot 728 that receives proximal ends of tooth gantries 734, 738. The proximal ends of the tooth gantries are adapted to slide in the horizontally extending slot 728 for making horizontal adjustments and positioning the tooth gantries. The VDO jig 720 includes a second vertically extending plate 724 having a vertically extending slot 755 that allows the horizontally extending plate 726 to slide up and down in the vertical slot 728 for making vertical adjustments to the positions of the tooth gantries. The lower end of the vertical plate 724 has an opening that receives the TAD gantry 730 for allowing the TAD gantry to slide toward and away from the mandible of a patient. After adjustments have been made, locking screws may be tightened for holding the positions of the various parts of the VDO jig 720.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A vertical dimension of occlusion jig used in all-on-4 dental procedures comprising:
    a vertical support column having an upper end, a lower end, and a longitudinal axis that extends between the upper and lower ends;
    a lateral arm support base coupled with said vertical support column, said lateral arm support base being configured to slide along and rotate about the longitudinal axis of said vertical support column;
    a first lateral support arm having a proximal end pivotally coupled with said lateral arm support base, a distal end spaced from the proximal end, and a longitudinal axis extending between the proximal and distal ends thereof;
    a first tooth gantry having a proximal end coupled with said first lateral support arm and a distal end spaced therefrom, wherein the proximal end of said first tooth gantry is adapted to slide along and rotate about the longitudinal axis of said first lateral support arm;
    a second lateral support arm having a proximal end pivotally coupled with said lateral arm support base, a distal end spaced from the proximal end, and a longitudinal axis extending between the proximal and distal ends thereof, wherein said first and second lateral support arms are configured to pivot relative to one another at the proximal ends thereof;
    a second tooth gantry having a proximal end coupled with said second lateral support arm and a distal end spaced therefrom, wherein the proximal end of said second tooth gantry is adapted to slide along and rotate about the longitudinal axis of said second lateral support arm;
    a temporary anchorage device (TAD) gantry coupled with said vertical support column, said vertical support column having an opening, wherein said TAD gantry has a shaft that passes through the opening in said vertical support column and is configured to slide along a longitudinal axis that is perpendicular to the longitudinal axis of said vertical support column.

2. The vertical dimension of occlusion jig as claimed in claim 1, further comprising a lateral arm support base fastener having a first position in which said lateral arm support base is free to slide along and rotate relative to the longitudinal axis of said vertical support column and a second position in which said lateral arm support base is locked in position and prevented from sliding along and rotating relative to the longitudinal axis of said vertical support column, wherein said lateral arm support base and said TAD gantry are spaced from one another along the longitudinal axis of said vertical support column, and wherein the spacing between said lateral arm support base and said TAD gantry is vertically adjustable along the length of said vertical support column when said lateral arm support base fastener is in the first position.

3. The vertical dimension of occlusion jig as claimed in claim 1, further comprising a lateral support arm fastener having a first position in which said first and second lateral support arms are free to pivot relative to said lateral arm support base and a second position in which said first and second lateral support arms are locked in place and prevented from pivoting relative to said lateral arm support base.

4. The vertical dimension of occlusion jig as claimed in claim 1, further comprising a TAD gantry fastener having a first position in which said TAD gantry shaft is free to slide along the longitudinal axis that is perpendicular to the longitudinal axis of said vertical support column and a second position in which said TAD gantry shaft is locked in place and prevented from sliding along the longitudinal axis that is perpendicular to the longitudinal axis of said vertical support column.

5. The vertical dimension of occlusion jig as claimed in claim 1, wherein the proximal end of said first tooth gantry has a first tooth gantry base coupled with said first lateral support arm, and wherein said first tooth gantry further comprises a first tooth gantry base fastener having a first position in which said first tooth gantry base is free to slide along and rotate about the longitudinal axis of said first lateral support arm and a second position in which said first tooth gantry base is locked in place and prevented from sliding along and rotating about the longitudinal axis of said first lateral support arm.

6. The vertical dimension of occlusion jig as claimed in claim 5, wherein said first tooth gantry further comprises:
    a first tooth gantry shaft coupled with said first tooth gantry base;
    a first tooth gantry shaft fastener having a first position in which said first tooth gantry shaft is extendable and retractable relative to said first tooth gantry base and a second position in which said first tooth gantry shaft is locked in place and is prevented from extending and retracting relative to said first tooth gantry base.

7. The vertical dimension of occlusion jig as claimed in claim 6, further comprising:
- a first tooth gantry socket coupled with a distal end of said first tooth gantry shaft;
- a first universal joint connecting said first tooth gantry socket with the distal end of said first tooth gantry shaft for enabling said first tooth gantry socket to rotate and pivot relative to the distal end of said first tooth gantry shaft.

8. The vertical dimension of occlusion jig as claimed in claim 7, further comprising a first universal joint fastener for said first tooth gantry socket having a first position in which said first tooth gantry socket is free to pivot relative to the distal end of said first tooth gantry shaft and a second position in which said first tooth gantry socket is locked in place and prevented from pivoting relative to the distal end of said first tooth gantry shaft.

9. The vertical dimension of occlusion jig as claimed in claim 8, further comprising a second universal joint fastener for said first tooth gantry socket having a first position in which said first tooth gantry socket is free to rotate relative to the distal end of said first tooth gantry shaft and a second position in which said first tooth gantry socket is locked in place and prevented from rotating relative to the distal end of said first tooth gantry shaft.

10. The vertical dimension of occlusion jig as claimed in claim 1, wherein the proximal end of said second tooth gantry has a second tooth gantry base coupled with said second lateral support arm, and wherein said second tooth gantry further comprises a second tooth gantry base fastener having a first position in which said second tooth gantry base is free to slide along and rotate about the longitudinal axis of said second lateral support arm and a second position in which said second tooth gantry base is locked in place and prevented from sliding along and rotating about the longitudinal axis of said second lateral support arm.

11. The vertical dimension of occlusion jig as claimed in claim 10, wherein said second tooth gantry further comprises:
- a second tooth gantry shaft coupled with said second tooth gantry base;
- a second tooth gantry shaft fastener having a first position in which said second tooth gantry shaft is extendable and retractable relative to said second tooth gantry base and a second position in which said second tooth gantry shaft is locked in place and is prevented from extending and retracting relative to said second tooth gantry base.

12. The vertical dimension of occlusion jig as claimed in claim 11, further comprising:
- a second tooth gantry socket coupled with a distal end of said second tooth gantry shaft;
- a second universal joint connecting said second tooth gantry socket with the distal end of said second tooth gantry shaft for enabling said second tooth gantry socket to rotate and pivot relative to the distal end of said second tooth gantry shaft.

13. The vertical dimension of occlusion jig as claimed in claim 12, further comprising a first universal joint fastener for said second tooth gantry socket having a first position in which said second tooth gantry socket is free to pivot relative to the distal end of said second tooth gantry shaft and a second position in which said second tooth gantry socket is locked in place and prevented from pivoting relative to the distal end of said second tooth gantry shaft.

14. The vertical dimension of occlusion jig as claimed in claim 13, further comprising a second universal joint fastener for said second tooth gantry socket having a first position in which said first tooth gantry socket is free to rotate relative to the distal end of said first tooth gantry shaft and a second position in which said first tooth gantry socket is locked in place and prevented from rotating relative to the distal end of said first tooth gantry shaft.

15. The vertical dimension of occlusion jig as claimed in claim 1, wherein said TAD gantry further comprises:
- a TAD gantry socket coupled with a distal free end of said TAD gantry shaft;
- a TAD gantry universal joint connecting said TAD gantry socket with the distal free end of said TAD gantry shaft for enabling said TAD gantry socket to rotate and pivot relative to the distal free end of said TAD gantry shaft.

16. The vertical dimension of occlusion jig as claimed in claim 15, further comprising a first universal joint fastener for said TAD gantry socket having a first position in which said TAD gantry socket is free to pivot relative to the distal end of said TAD gantry shaft and a second position in which said TAD gantry socket is locked in place and prevented from pivoting relative to the distal end of said TAD gantry shaft.

17. The vertical dimension of occlusion jig as claimed in claim 16, further comprising a second universal joint fastener for said TAD gantry socket having a first position in which said TAD gantry socket is free to rotate relative to the distal end of said TAD gantry shaft and a second position in which said TAD gantry socket is locked in place and prevented from rotating relative to the distal end of said TAD gantry shaft.

18. The vertical dimension of occlusion jig as claimed in claim 2, wherein the vertical distance between said lateral arm support base and said TAD gantry is adjustable when said lateral arm support base fastener is in the first position and is not adjustable when said lateral arm support base fastener is in the second position.

19. The vertical dimension of occlusion jig as claimed in claim 1, wherein said jig is made of materials selected from the group consisting of metal, steel, stainless steel, alloys and polymers.

20. The vertical dimension of occlusion jig as claimed in claim 7, further comprising:
- a ball component attached to a tooth;
- said first tooth gantry socket being connected to said ball component for releasably securing said first tooth gantry to said tooth.

* * * * *